US012740561B2

(12) United States Patent
Huwyler et al.

(10) Patent No.: US 12,740,561 B2
(45) Date of Patent: Sep. 22, 2026

(54) HETEROCYCLIC COMPOUNDS FOR THE CONTROL OF INVERTEBRATE PESTS

(71) Applicant: BASF SE, Ludwigshafen (DE)

(72) Inventors: Nikolas Huwyler, Ludwigshafen (DE); Karsten Koerber, Ludwigshafen (DE); Erik Gilberg, Cologne (DE); Julia Pedroni, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 364 days.

(21) Appl. No.: 18/692,440

(22) PCT Filed: Sep. 9, 2022

(86) PCT No.: PCT/EP2022/075058

§ 371 (c)(1),
(2) Date: Mar. 15, 2024

(87) PCT Pub. No.: WO2023/041422

PCT Pub. Date: Mar. 23, 2023

(65) Prior Publication Data

US 2025/0000093 A1 Jan. 2, 2025

(30) Foreign Application Priority Data

Sep. 20, 2021 (EP) .................................... 21197584
Sep. 20, 2021 (EP) .................................... 21197585
Dec. 16, 2021 (EP) .................................... 21215022

(51) Int. Cl.

| | |
|---|---|
| ***A01N 43/653*** | (2006.01) |
| ***A01P 7/04*** | (2006.01) |
| ***A61K 31/497*** | (2006.01) |
| ***A61K 31/506*** | (2006.01) |
| ***C07D 401/04*** | (2006.01) |
| ***C07D 401/14*** | (2006.01) |
| ***C07D 403/04*** | (2006.01) |
| ***C07D 409/14*** | (2006.01) |

(52) U.S. Cl.

CPC .............. *A01N 43/653* (2013.01); *A01P 7/04* (2021.08); *A61K 31/497* (2013.01); *A61K 31/506* (2013.01); *C07D 401/04* (2013.01); *C07D 401/14* (2013.01); *C07D 403/04* (2013.01); *C07D 409/14* (2013.01)

(58) Field of Classification Search

None

See application file for complete search history.

(56) References Cited

FOREIGN PATENT DOCUMENTS

WO WO-02/100846 A1 12/2002
WO WO-2021/037614 A1 3/2021

OTHER PUBLICATIONS

El-Faham, et al., "Peptide Coupling Reagents, More than a Letter Soup", Chemical Reviews, vol. 111, Issue 11, Aug. 26, 2011, pp. 6557-6602.

European Patent Application No. 21197584.2, Extended European Search Report, dated Feb. 15, 2022.

Helferich, et al., "n-butyryl Chloride", Organic Syntheses, vol. 9, 1929, pp. 32.

International Application No. PCT/EP2022/075058, International Search Report, mailed Dec. 22, 2022.

Somagond, et al., "Design, synthesis, docking and in vitro antifungal study of 1, 2, 4-triazole hybrids of 2-(aryloxy) quinolines", Heterocyclic Communications, vol. 23, Issue 4, Jul. 19, 2017, pp. 317-324.

*Primary Examiner* — Samantha L Shterengarts

(74) *Attorney, Agent, or Firm* — MARSHALL, GERSTEIN & BORUN LLP

(57) ABSTRACT

The invention relates to compounds of formula (I) wherein the variables have the meanings as defined in the specification, to compositions comprising them, to active compound combinations comprising them, and to their use for protecting growing plants and animals from attack or infestation by invertebrate pests, furthermore, to seed comprising such compounds.

(I)

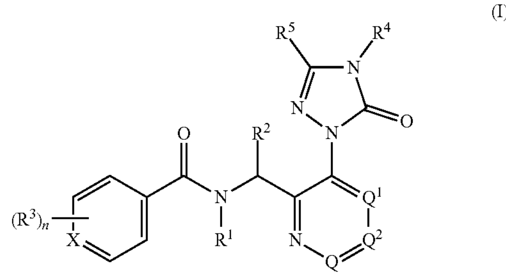

19 Claims, No Drawings

HETEROCYCLIC COMPOUNDS FOR THE CONTROL OF INVERTEBRATE PESTS

CROSS-REFERENCE TO RELATED APPLICATIONS

This is the U.S. national phase of International Application No. PCT/EP2022/075058, filed Sep. 9, 2022, which claims the benefit of European Patent Application No. 21197584.2, filed Sep. 20, 2021, European Patent Application 21197585.9, filed Sep. 20, 2021, and European Patent Application No. 21215022.1, filed Dec. 16, 2021.

The invention relates to compounds of formula I

I

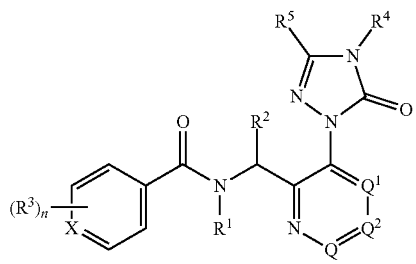

wherein $R^1$ is H, OH, $C_1$-$C_6$-alkyl, $C_1$-$C_6$-haloalkyl, $C_3$-$C_6$-cycloalkyl, $C_3$-$C_6$-halocycloalkyl, $C_1$-$C_5$-alkoxy, $C_2$-$C_4$-alkenyl, $C_2$-$C_4$-alkynyl, $C_1$-$C_4$-alkyl-$C_3$-$C_6$-cycloalkyl, $C_1$-$C_4$-alkyl-$C_3$-$C_6$-halocycloalkyl, which groups are unsubstituted, or partially or fully substituted with $R^1$; or $C(=N—R^{11})R^{12}$, $C(O)R^{11a}$;

$R^{11}$ is CN, $NO_2$, $NR^{12}R^{13}$, $C(O)NH_2$, $C(S)NH_2$, C(O)OH, $OR^{14}$, $Si(CH_3)_3$; $C_1$-$C_6$-alkyl; $C_1$-$C_6$-haloalkyl; $C_2$-$C_6$-alkenyl; $C_2$-$C_6$-haloalkenyl; $C_2$-$C_6$-alkynyl; $C_2$-$C_6$-haloalkynyl; $C_3$-$C_4$-cycloalkyl-$C_1$-$C_2$-alkyl, which ring is unsubstituted or substituted with 1 or 2 halogen; 3- to 6-membered heterocyclyl, 5- or 6-membered hetaryl, or phenyl, which rings are unsubstituted or substituted with halogen, $C_1$-$C_3$-haloalkyl, and/or CN;

$R^{11a}$ is $NR^{12}R^{13}$, $C(O)NH_2$, $C(S)NH_2$, C(O)OH, $OR^{14}$, $Si(CH_3)_3$; $C_1$-$C_6$-haloalkyl; $C_2$-$C_6$-alkenyl; $C_2$-$C_6$-haloalkenyl; $C_2$-$C_6$-alkynyl; $C_2$-$C_6$-haloalkynyl; $C_3$-$C_6$-cycloalkyl-$C_1$-$C_2$-alkyl, which ring is unsubstituted or substituted with 1 or 2 halogen; 3- to 6-membered heterocyclyl, which rings are unsubstituted or substituted with halogen, $C_1$-$C_3$-haloalkyl, and/or CN;

$R^{12}$, $R^{13}$ are independently from each other H, $C_1$-$C_4$-alkyl, $C_1$-$C_4$-alkoxy, $C_1$-$C_4$-haloalkoxy, $C_1$-$C_4$-haloalkyl, $C_3$-$C_6$-cycloalkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, $C(O)NR^{121}R^{131}$, $S(O)_m$—$C_1$-$C_4$-haloalkyl, $S(O)_m$—$C_3$-$C_6$-cycloalkyl, $S(O)_m$—$C_3$-$C_6$-halocycloalkyl; 3- to 6-membered heterocyclyl, 5- or 6-membered hetaryl, or phenyl, which rings are unsubstituted or substituted with halogen, $C_1$-$C_3$-haloalkyl, and/or CN;

$R^{121}$ and $R^{131}$ are independently from each other H, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy; $C_1$-$C_4$-alkyl-phenyl, $C_1$-$C_4$-alkyl-3-6-membered hetaryl, phenyl, 3- to 6-membered heterocyclyl or 5- or 6-membered hetaryl, which rings are unsubstituted or substituted with halogen, $C_1$-$C_3$-haloalkyl, and/or CN; or $R^{121}$ and $R^{131}$ together with the nitrogen atom they are bound to form a 3-6 membered saturated, partially or fully unsaturated heterocycle, which may further contain 1 or 2 heteroatoms ring members selected from N, O and S, wherein S may be oxidized, which heterocycle is unsubstituted or substituted with halogen, $C_1$-$C_3$-haloalkyl, and/or CN;

or $R^{12}$ and $R^{13}$ together with the nitrogen atom they are bound to form a 3-6 membered saturated, partially unsaturated, or aromatic heterocycle, which may contain 1 or 2 additional heteroatoms selected from N, O and S, wherein S may be partially or fully oxidized, and which is unsubstituted or substituted with oxo, and/or $R^3$;

or $R^{12}$ and $R^{13}$ together with the nitrogen atom they are bound to form a group $N=S(=O)R^{14a}R^{14b}$, wherein $R^{14a}$ and $R^{14b}$ are defined as $R^{14}$;

m is 0, 1, or 2;

$R^{14}$ is H, $C_1$-$C_4$-alkyl, $C_1$-$C_4$-haloalkyl, $C_3$-$C_6$-cycloalkyl, $C_3$-$C_6$-halocycloalkyl, $C_3$-$C_4$-cycloalkyl-$C_1$-$C_2$-alkyl, $C_3$-$C_4$-halocycloalkyl-$C_1$-$C_2$-alkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, or phenyl which is unsubstituted or partially or fully substituted with $R^3$;

$R^2$ is H, CN, $C_1$-$C_3$-alkyl, $C_1$-$C_3$-haloalkyl, $C_2$-$C_3$-alkynyl;

X is CH, $CR^3$, or N;

$R^3$ is halogen, CN, $NO_2$, $C_1$-$C_4$-alkyl, $C_3$-$C_6$-cycloalkyl, $C_1$-$C_6$-haloalkyl, $C_3$-$C_6$-halocycloalkyl, $OR^{14}$, $S(O)_m$—$R^{14}$; which are unsubstituted or substituted with $R^{3a}$;

$R^{3a}$ halogen, CN, $NO_2$, $C_1$-$C_4$-alkyl, $C_1$-$C_4$-haloalkyl, $C_1$-$C_4$-alkoxy-$C_1$-$C_4$-alkyl, $OR^{15}$, $C_1$-$C_4$-haloalkoxy, $C_3$-$C_4$-cycloalkyl, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl;

n is 0, 1, 2, or 3;

$R^4$ is $C_1$-$C_6$-alkyl, $C_3$-$C_6$-cycloalkyl, $C_1$-$C_6$-haloalkyl, $C_3$-$C_6$-halocycloalkyl, $C_2$-$C_4$-alkenyl, $C_2$-$C_4$-haloalkenyl, $C_2$-$C_4$-alkynyl, each unsubstituted or partially or fully substituted with $R^{41}$; $S(O)_m$—$C_1$-$C_4$-alkyl, $S(O)_m$—$C_1$-$C_4$-haloalkyl, $S(O)_m$—$C_3$-$C_6$-cycloalkyl, $S(O)_m$—$C_3$-$C_6$-halocycloalkyl, $NR^{12}R^{13}$, $C(O)NR^{12}R^{13}$, $C(O)OR^{14}$, 3- to 6-membered heterocyclyl, 5- or 6-membered hetaryl, or phenyl, which rings are unsubstituted or partially or fully substituted with $R^3$;

$R^{41}$ is H, $OR^{15}$, $NR^{12}R^{13}$, $C_1$-$C_4$-alkyl, $C_1$-$C_4$-haloalkyl, $C_3$—C-cycloalkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, $C(O)OR^{15}$, $C(O)NR^{121}R^{131}$; $S(O)_m$—$C_1$-$C_4$-haloalkyl, $S(O)_m$—$C_3$-$C_4$-cycloalkyl, $S(O)_m$—$C_3$-$C_4$-halocycloalkyl; 3- to 6-membered heterocyclyl, 5- or 6-membered hetaryl, or phenyl;

which cyclic $R^{41}$ groups are unsubstituted or partially or fully substituted with halogen, $C_1$-$C_3$-haloalkyl, and/or CN;

$R^{15}$ is H, $C_1$-$C_4$-alkyl, or $C_1$-$C_4$-haloalkyl, $C_3$-$C_6$-cycloalkyl, $C_1$-$C_6$-halocycloalkyl, which carbon chains are unsubstituted or partially or fully substituted with $R^{11}$; or 3- to 6-membered heterocyclyl, 5- or 6-membered hetaryl, or phenyl, which rings are unsubstituted or partially or fully substituted with $R^3$;

$R^5$ is H, halogen, CN, $OR^{15}$, $C_1$-$C_6$-alkyl, $C_1$-$C_6$-haloalkyl, $C_1$-$C_6$-alkoxy, $C_3$-$C_6$-cycloalkyl, $C_1$-$C_4$-alkyl-phenyl, $C_1$-$C_4$-alkyl-3-6-membered hetaryl, phenyl, 3- to 6-membered heterocyclyl or 5- or 6-membered hetaryl, which rings are unsubstituted or substituted with halogen, $C_1$-$C_3$-haloalkyl, and/or CN;

Q, $Q^1$, and $Q^2$ are, independently from each other, N or $CR^6$, wherein no more than one of Q, $Q^1$, and $Q^2$ is N;

$R^6$ is H, halogen, CN, $OR^{14}$, $NR^{12}R^{13}$, $C_1$-$C_4$-alkyl, $C_1$-$C_4$-haloalkyl, $C_3$-$C_6$-cycloalkyl, $C_3$-$C_6$halocycloalkyl, $C(O)NR^{12}R^{13}$, $C(O)OR^{14}$, $S(O)_m$—$C_1$-$C_4$-alkyl, $S(O)_m$—$C_1$-$C_4$-haloalkyl, $S(O)_mC_3$-$C_6$-cycloalkyl, $S(O)_m$—$C_3$-$C_6$-halocycloalkyl;

and the N-oxides, stereoisomers and agriculturally or veterinarily acceptable salts thereof.

The invention also provides agricultural compositions comprising at least one compound of formula I, a stereoisomer thereof and/or an agriculturally acceptable salt thereof and at least one liquid and/or solid carrier, especially at least one inert liquid and/or solid agriculturally acceptable carrier.

The invention also provides a veterinary composition comprising at least one compound of formula I, a stereoisomer thereof and/or a veterinarily acceptable salt thereof and at least one liquid and/or solid carrier, especially at least one inert veterinarily liquid and/or solid acceptable carrier.

The invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The invention also relates to plant propagation material, in particular seed, comprising at least one compound of formula I and/or an agriculturally acceptable salt thereof.

The invention further relates to a method for treating or protecting an animal from infestation or infection by parasites which comprises bringing the animal in contact with a parasiticidally effective amount of a compound of formula I or a veterinarily acceptable salt thereof. Bringing the animal in contact with the compound I, its salt or the veterinary composition of the invention means applying or administering it to the animal.

WO 2017/192385, WO2021/068179, WO2021/069575, and WO2021/037614 describe structurally closely related active compounds. These compounds are mentioned to be useful for combating invertebrate pests.

Nevertheless, there remains a need for highly effective and versatile agents for combating invertebrate pests. It is therefore an object of the invention to provide compounds having a good pesticidal activity and showing a broad activity spectrum against a large number of different invertebrate pests, especially against difficult to control pests, such as insects.

It has been found that these objects can be achieved by compounds of formula I as depicted and defined below, and by their stereoisomers, salts, tautomers and N-oxides, in particular their agriculturally acceptable salts.

Compounds I with $R^1$ being different from H can be obtained by reaction of a compound II in which $R^1$=H with a suitable reagent III. In formula III, R has the same meaning as $R^1$ in formula I, respectively, and Y is a nucleophilic leaving group, such as a halide, mesylate, or tosylate, preferably Br or Cl. The reaction can be effected under conditions known from literature.

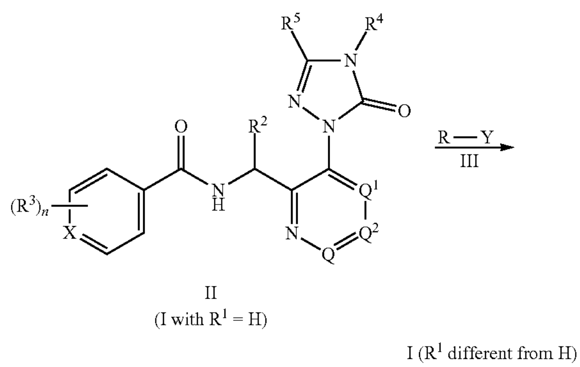

II
(I with $R^1$ = H)

I ($R^1$ different from H)

This transformation is usually carried out at temperatures from −10° C. to +110° C., preferably from 0° C. to 25° C., in an inert solvent and in the presence of a base [cf. WO 2002100846 and S. M. Somagond, Heterocycl. Commun. 2017, 317].

The starting materials are generally reacted with one another in equimolar amounts. In terms of yield, it may be advantageous to employ an excess of Ill, based on 11.

Compounds II can be obtained by reaction of an amino compound IV with a carboxylic acid V

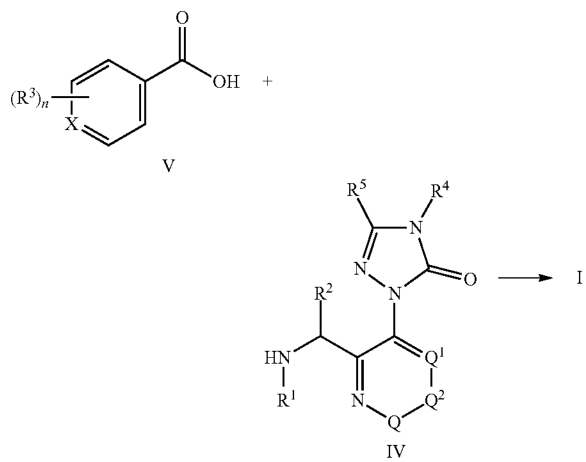

V

IV

I

This transformation is usually carried out at temperatures of from −20° C. to 50° C., preferably from 0° C. to 25° C., in an inert solvent, in the presence of a peptide coupling reagent and optionally in the presence of a base [cf. A. El-Faham, Chem. Rev. 2011, 6557], or in two steps by preparation of an intermediate acyl chloride from V under conditions known from literature, e.g. by reaction with $SOCl_2$ or oxalyl chloride in dimethylformamide (DMF) (cf. Schaefer et al, Organic Syntheses 1929, 32), followed by reaction with IV in the presence of a base, optionally under Schotten-Baumann conditions (Baumann, Chem. Ber. 1886, 3218). Suitable peptide coupling reagents are, e.g., dicyclohexylcarbodiimide, diisopropylcarbodiimide, 1-ethyl-3-(3'-dimethylaminopropyl)carbodiimide hydrochloride, or chloro-N,N,N',N'-tetramethylformamidinium hexafluorophosphate, which are commonly used together with catalytic, stoichiometric, excess amounts of additives, such as 1-hydroxybenzotriazole, 1-hydroxy-7-aza-benzotriazole, 4-(dimethylamino)pyridine, and/or 1-methylimidazole.

Suitable solvents are halogenated hydrocarbons, such as dichloromethane (DCM) or 1,2-dichloroethane, ethers, such as diethylether, tetrahydrofurane (THF) or 1,4-dioxane, or high-boiling solvents such as DMF, preferably DCM or DMF, or in aqueous media.

Suitable bases are, in general, inorganic compounds, such as alkali metal and alkaline earth metal hydroxides, such as LiOH, NaOH, KOH, or $Ca(OH)_2$, alkali metal and alkaline earth metal carbonates, such as $Na_2CO_3$, $K_2CO_3$, or $Cs_2CO_3$, alkali metal bicarbonates, such as $NaHCO_3$, or organic bases, for example tertiary amines, such as triethylamine, diisopropylethylamine, N-methylpiperidine, or basic aromatic rings, such as pyridine, 2,4,6-collidine, 2,6-lutidine, or 4-(dimethylamino)pyridine, or bicyclic amines, such as 1,8-diazabicylo[5.4.0]undec-7-ene (DBU), 1,5-diazabicyclo[4.3.0]non-5-ene (DBN), or 1,4-diazabicyclo[2.2.2]octane (DABCO).

Particular preference is given to triethylamine, diisopropylethylamine, and NaOH.

The bases are generally employed in stoichiometric or excess amounts; however, they can also be used in catalytic amounts or, if appropriate, as the solvent.

The starting materials are generally reacted with one another in equimolar amounts. In terms of yield, it may be advantageous to employ an excess of IV based on V.

Compounds IV can be obtained by reductive amination of a compound VI.

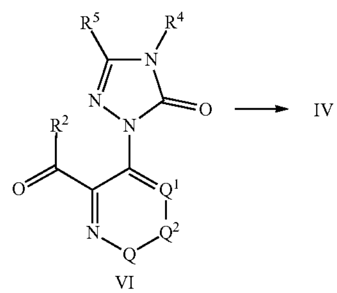

VI → IV

This transformation is usually carried out at temperatures of from 0° C. to 130° C., preferably from 20° C. to 70° C., generally in alcoholic and/or aqueous media and in the presence of a reagent and a reducing agent [cf. WO2021037614]. Suitable solvents are alcohols, such as methanol, ethanol, n-propanol, 2-propanol, or n-butanol, or water, preferably methanol. It is also possible to use mixtures of the aforementioned solvents. Suitable reagents are ammonium acetate ($NH_4Ac$), ammonium formate, $NH_4OH$, $NH_4Cl$, ammonia, or primary amines $R^1NH_2$. Suitable reducing agents are $NaBH_3CN$, sodium triacetoxyborohydride, or $NaBH_4$. Preference is given to ammonium acetate and $NaBH_3CN$, resp.

Compounds VI are obtainable from compounds VII in a two-step sequence consisting of Stille coupling of VII with an alkoxyalkenylstannane such as VIII followed by hydrolysis of the resulting enol ether moiety to the ketone VI.

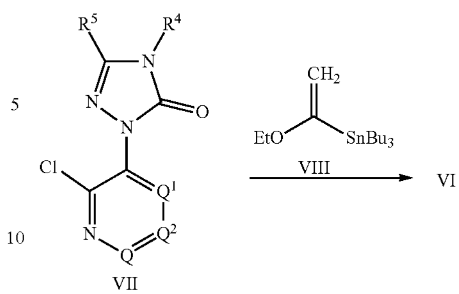

VII VIII VI

The Stille coupling reaction is usually carried out at temperatures from 50° C. to 150° C., preferably from 70° C. to 120° C., in an inert solvent in the presence of one or more catalysts and optionally in the presence of one or more additives and a base [cf. H. Lin et al., Bioorg Med Chem Lett 2010, 679]. Suitable solvents are aromatic hydrocarbons such as toluene, o-, m-, p-xylene, and mesitylene, or ethers such as THF and 1,4-dioxane, preferably toluene or 1,4-dioxane. It is also possible to use mixtures of the aforementioned solvents. Suitable catalysts are palladium complexes, such as tetrakis(triphenylphosphine)palladium, tris(dibenzylideneacetone)dipalladium, palladium diacetate, dichlorobis(triphenylphosphine)palladium, and [1,1'-bis(diphenylphosphino)ferrocene]dichloropalladium, preferably dichlorobis(triphenylphosphine)palladium. Further suitable optional catalysts are common ligands, such as dicyclohexyl [2',4',6'-tris(propan-2-yl)[1,1'-biphenyl]-2-yl]phosphine or triphenylphosphine. Suitable additives are, in general, inorganic compounds, such as cesium fluoride and cuprous iodide. The starting materials are generally reacted with one another in equimolar amounts. In terms of yield, it may be advantageous to employ an excess of VIII, based on VII.

The hydrolysis is usually carried out at temperatures from −20° C. to 40° C., preferably from 0° C. to 25° C., in aqueous acidic media containing aqueous HCl at concentrations between 0.5M and 3M and optionally containing an organic solvent such as acetonitrile, acetone, THF, or methanol (cf H. Lin et al., Bioorg. Med. Chem. Lett. 2010, 679).

Alternatively, compounds VI wherein $Q^1$=N and $Q^2$=Q=CH can be obtained by reaction of 1-(3-chloropyrazin-2-yl)ethanone with 1H-1,2,4-triazol-5-ones in the presence of a base, such as $Cs_2CO_3$ or $K_2CO_3$, in an aprotic polar solvent, such as acetonitrile, DMF, or dimethyl sulfoxide (DMSO), at temperatures from 0° C. to 150° C., preferably from 60° C. to 120° C., in analogy to WO2017055185 and WO2020178789. While 1-(3-chloropyrazin-2-yl)ethanone is known from WO2021259997, the preparation of 1H-1,2,4-triazol-5-ones is well described in the literature, e.g. in WO2017205709.

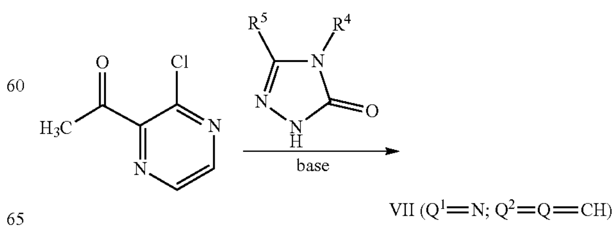

VII ($Q^1$=N; $Q^2$=Q=CH)

Compounds VII are obtainable from triazolones IX. In formula X, group Z is a leaving group, e.g. a halide, such as I, Br, and Cl, or a sulfonate, such as triflate or mesylate.

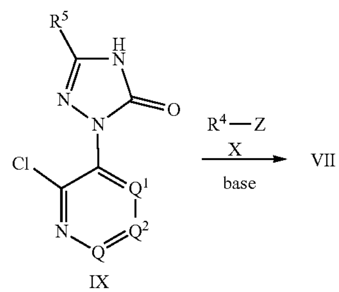

IX

VII

This transformation is usually carried out at temperatures from 0° C. to 120° C., preferably from 25° C. to 70° C., in an inert solvent and in the presence of a base [cf. A. R. Nesaragi et al., Bioorg. Med. Chem. Lett. 2021, 127984]. Suitable solvents are halogenated hydrocarbons, such as DCM, 1,2-dichloroethane, or chloroform, ethers, such as diethylether, tert-butylmethylether, dioxane, or THF, nitriles, such as acetonitrile or propionitrile, and polar aprotic solvents, such as DMSO, DMF, or dimethylacetamide (DMA), preferably acetonitrile. It is also possible to use mixtures of the aforementioned solvents.

Suitable bases are, in general, inorganic compounds, such as alkali metal carbonates, such as $Na_2CO_3$, $K_2CO_3$, or $Cs_2CO_3$, alkali metal hydroxides, such as NaOH or KOH, or organic bases, e.g. tertiary amines such as triethylamine or diisopropylethylamine. Preference is given to $K_2CO_3$. The bases are generally employed in equimolar amounts; however, they can also be used in excess or, if appropriate, as solvent.

The starting materials are generally reacted with one another in equimolar amounts. In terms of yield, it may be advantageous to employ an excess of X, based on IX.

Triazolones IX are obtainable from compounds XI by reaction with diphenylphosphoryl azide or similar reagent (e.g. employing a mixture of trimethylsilyl azide and propanephosphonic acid anhydride) using an aromatic hydrocarbon, such as benzene, toluene, xylenes, or mesitylene, as a solvent, and a tertiary amine, such as triethylamine or diisopropylethylamine, as a base, at temperatures from 0° C. to 130° C., preferably between 25° C. and 80° C., as known from literature (cf. J. W. Lyga, Synth. Commun. 1986, 163).

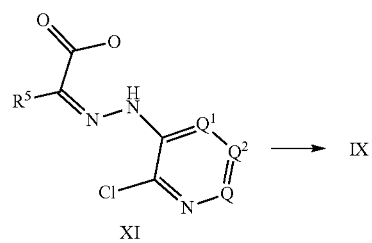

XI

IX

Compounds XI are obtainable from hydrazines XII by condensation with the aldehyde or ketone moiety of a 1,2-dicarbonyl compound XIII.

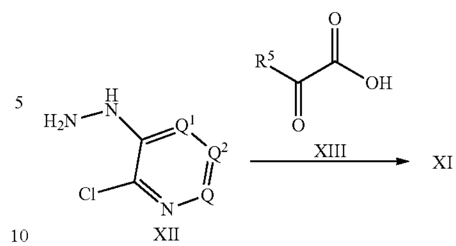

XII

XI

This transformation is usually carried out at temperatures from 0° C. to 110° C., preferably from 25° C. to 90° C., in a protic solvent, such as methanol, ethanol, 2-propanol, water, or a mixture of the aforementioned solvents, preferably in water, and optionally in the presence of an acid, such as acetic acid or HCl (c.f. Q. Yang et al., Org. Process Res. Dev. 2019, 2122).

The starting materials are generally reacted with one another in equimolar amounts. In terms of yield, it may be advantageous to employ an excess of XIII, based on XII.

Compounds XII are either commercially available, e.g., CAS 63286-28-2 and 117087-45-3, or can be prepared from commercially available materials under conditions known from literature.

Alternatively, compounds I can be obtained from 4-methoxybenzyl- (PMB-) substituted compounds I ($R^4$=PMB) in a two-step sequence involving removal of the PMB group by treatment with an acid, such as TFA (e.g., WO2007134862) or with an oxidizing agent such as diammonium cerium(IV) nitrate (CAN, e.g., WO2017167832), followed by reaction of the intermediate (INT) using the reagents and reaction conditions as described above for the synthesis of compounds VII from compounds IX. The same two-step sequence can also be used to obtain compounds I from the corresponding compounds I wherein $R^4$ is 2,4-dimethoxybenzyl (DMB) or 2,4,6-trimethoxybenzyl (TMB). Intermediate compounds (INT) are novel. The variables in formula (INT) are as defined for formula I.

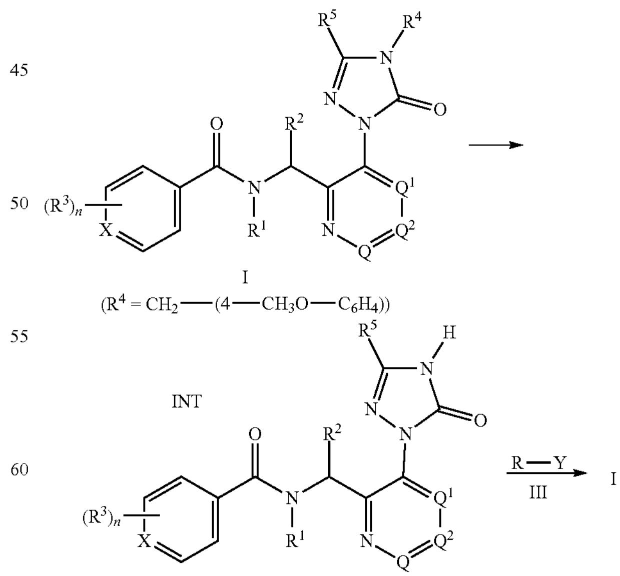

I ($R^4 = CH_2—(4—CH_3O—C_6H_4)$)

INT

I

The reaction mixtures are worked up in a customary manner, e.g. by mixing with water, extracting with an appropriate organic solvent, separating the phases and, if appropriate, chromatographic purification of the crude products. Some of the intermediates and end products are obtained in the form of colourless or slightly brownish viscous oils which are purified or freed from volatile components under reduced pressure and at moderately elevated temperature. If the intermediates and end products are obtained as solids, purification can also be carried out by recrystallization or digestion.

If individual compounds I cannot be obtained by the routes described above, they can be prepared by derivatization of other compounds I.

However, if the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the pest to be controlled.

The organic moieties groups mentioned in the above definitions of the variables are—like the term halogen—collective terms for individual listings of the individual group members. The prefix $C_n$-$C_m$ indicates in each case the possible number of carbon atoms in the group.

The term "partially or fully substituted" by a radical means that in general the group is substituted with same or different radicals.

The term "halogen" denotes in each case fluorine, bromine, chlorine, or iodine, in particular fluorine, chlorine, or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl (Me), ethyl (Et), n-propyl (n-Pr), iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2dichloro-2-fluorethoxy, 2,2,2-trichloroethoxy, pentafluoroethoxy and the like.

The term "alkylthio "(alkylsulfanyl: S-alkyl)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom.

The term "haloalkylthio" as used herein refers to an alkylthio group as mentioned above wherein the hydrogen atoms are partially or fully substituted by fluorine, chlorine, bromine and/or iodine.

The term "alkylsulfinyl" (alkylsulfoxyl: S(═O)-alkyl), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "haloalkylsulfinyl" as used herein refers to an alkylsulfinyl group as mentioned above wherein the hydrogen atoms are partially or fully substituted by fluorine, chlorine, bromine and/or iodine.

The term "alkylsulfonyl" ($S(═O)_2$-alkyl) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "haloalkylsulfonyl" as used herein refers to an alkylsulfonyl group as mentioned above wherein the hydrogen atoms are partially or fully substituted by fluorine, chlorine, bromine and/or iodine.

The term "alkylcarbonyl" refers to an alkyl group as defined above, which is bonded via the carbon atom of a carbonyl group (C=O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkylcarbonyl group as defined above, which is bonded via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g.

vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methyl-but-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl ($cC_3H_5$), cyclobutyl ($cC_4H_7$), cyclopentyl ($cC_5H_9$), cyclohexyl ($cC_6H_{11}$), cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy and halocycloalkylthio denotes in each case a monocyclic cycloaliphatic radical having usually from 3 to 10 C atoms or 3 to 6 C atoms, wherein at least one, e.g. 1, 2, 3, 4 or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichloro-cyclopentyl and the like.

The term "halocycloalkenyl" as used herein and in the halocycloalkenyl moieties of halocyclo-alkenyloxy and halocycloalkenylthio denotes in each case a monocyclic singly unsaturated nonaromatic radical having usually from 3 to 10, e.g. 3 or 4 or from 5 to 10 carbon atoms, preferably from 3- to 8 carbon atoms, wherein at least one, e.g. 1, 2, 3, 4 or 5 of the hydrogen atoms, are replaced by halogen, in particular by fluorine or chlorine. Examples are 3,3-difluorocyclopropen-1-yl and 3,3-dichlorocyclopropen-1-yl.

The term "cycloalkenylalkyl" refers to a cycloalkenyl group as defined above which is bonded via an alkyl group, such as a $C_1$-$C_5$-alkyl group or a $C_1$-$C_4$-alkyl group, in particular a methyl group (=cycloalkenylmethyl), to the remainder of the molecule.

The term "carbocycle" or "carbocyclyl" includes in general a 3- to 12-membered, preferably a 3- to 8-membered or a 5- to 8-membered, more preferably a 5- or 6-membered mono-cyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above.

The term "heterocycle" or "heterocyclyl" includes in general 3- to 12-membered, preferably 3- to 6-membered, in particular 6-membered monocyclic heterocyclic non-aromatic radicals. The heterocyclic non-aromatic radicals usually comprise 1, 2, 3, 4 or 5, preferably 1, 2 or 3 heteroatoms selected from N, O, and S as ring members, wherein S-atoms as ring members may be present as S, SO, or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S. oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-only, and the like.

The term "hetaryl" includes monocyclic 5- or 6-membered heteroaromatic radicals comprising as ring members 1, 2, 3 or 4 heteroatoms selected from N, O, and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O, and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocyclylalkyl" and "hetarylalkyl" refer to heterocyclyl or hetaryl, respectively, as defined above which are bonded via a $C_1$-$C_5$-alkyl group or a $C_1$-$C_4$-alkyl group, in particular a methyl group (=heterocyclylmethyl or hetarylmethyl, respectively), to the remainder of the molecule.

The term "arylalkyl" and "phenylalkyl" refer to aryl as defined above and phenyl, respectively, which are bonded via $C_1$-$C_5$-alkyl group or a $C_1$-$C_4$-alkyl group, in particular a methyl group (=arylmethyl or phenylmethyl), to the remainder of the molecule, examples including benzyl, 1-phenylethyl, 2-phenylethyl, 2-phenoxyethyl etc.

The terms "alkylene", "cycloalkylene", "heterocycloalkylene", "alkenylene", "cycloalkenylene", "heterocycloalkenylene" and "alkynylene" refer to alkyl, cycloalkyl, heterocycloalkyl, alkenyl, cycloalkenyl, heterocycloalkenyl and alkynyl as defined above, respectively, which are bonded to the remainder of the molecule, via two atoms, preferably via two carbon atoms, of the respective group, so that they represent a linker between two moieties of the molecule.

In a particular embodiment, the variables of the compounds of the formula I have the following meanings, these meanings, both on their own and in combination with one another, being particular embodiments of the compounds of the formula I.

Embodiments and preferred compounds of the invention for use in pesticidal methods and for insecticidal application purposes are outlined in the following paragraphs.

With respect to the variables, the particularly preferred embodiments of the intermediates correspond to those of the compounds of the formula I.

In a preferred embodiment, the compounds I are present in form of a mixture of compounds I.A and I.B, wherein compound I.A with S-configuration of the carbon atom neighboring the nitrogen is present in an amount of more than 50% by weight, in particular of at least 70% by weight, more particularly of at least 85% by weight, specifically of at least 90% by weight, based on the total weight of compounds I.A and I.B.

I.A

I.B

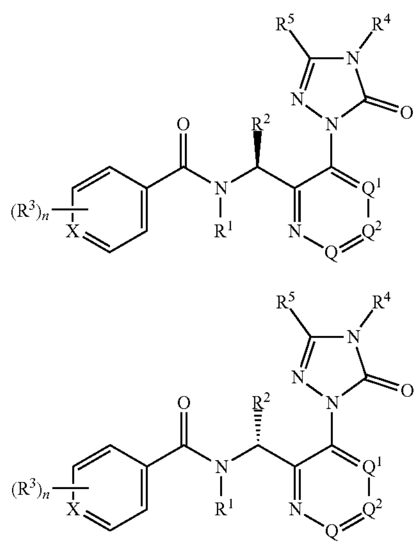

In one particularly preferred embodiment of the invention, the method comprises the step of contacting the plant, parts of it, its propagation material, the pests, their food supply, habitat or breeding grounds with a pesticidally effective amount of a compound of formula I.A.

Preferably $R^1$ is H, $C_1$-$C_6$-alkyl, $C_3$-$C_6$-alkynyl, $C_3$-$C_6$-cycloalkyl, or $C_1$-$C_4$-alkyl-$C_3$-$C_6$-cycloalkyl which rings are unsubstituted or substituted with CN or halogen.

Preferably $R^2$ is $CH_3$.

In formula I preferably $Q^1$ is N and Q and $Q^2$ are CH. Such compounds correspond to formula I.a.

In a preferred embodiment of formula I compounds Q is CH or $CR^6$, particularly Q is CH.

In another embodiment Q is $CR^6$, wherein $R^5$ is halogen, particularly Cl. In another embodiment Q is $CR^6$, wherein $R^6$ is $C_1$-$C_4$-alkyl, particularly $CH_3$.

In another embodiment of formula I Q is C—$R^6$, wherein $R^6$ is preferably H, halogen, or $C_1$-$C_4$-alkyl, particularly H or halogen. Such compounds correspond to formula I.b.

In a preferred embodiment of formula I.b $Q^1$ is N and $Q^2$ is CH.

in another preferred embodiment of formula I.b $Q^1$ and $Q^2$ are CH.

I.a

I.b

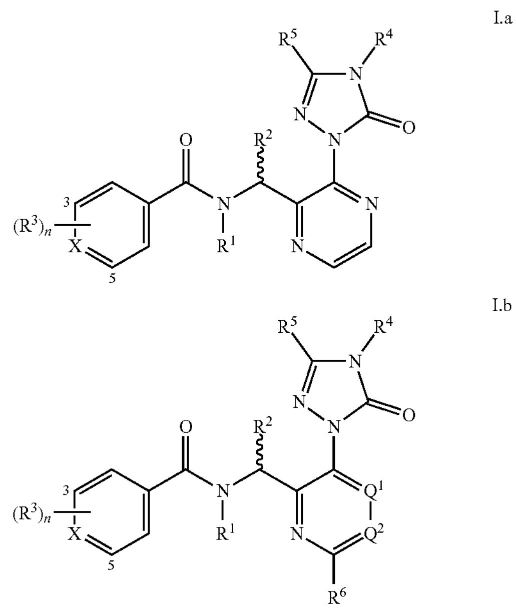

In formula I X is preferably CH or $CR^3$, particularly CH. Such compounds correspond to Formula I.1

I.1

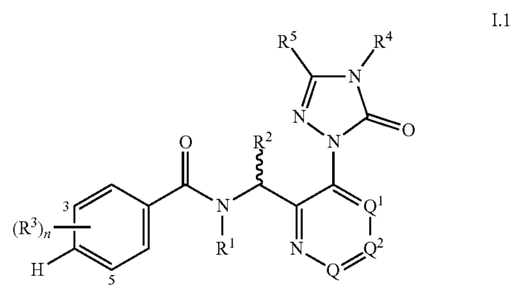

In another embodiment of formula I X is N. Such compounds correspond to formula I.2.

I.2

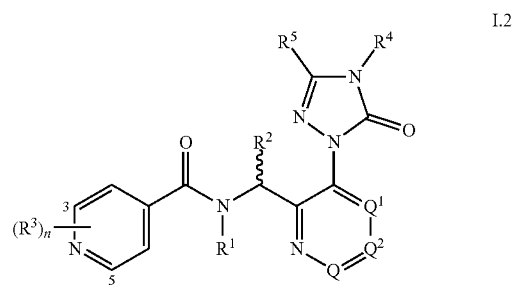

$R^3$ is preferably halogen, CN, $C_1$-$C_4$-haloalkyl, $C_1$-$C_4$-haloalkoxy, $C_3$-$C_4$-cycloalkyl unsubstituted or substituted with one or more CN, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl, which rings are unsubstituted or substituted with CN or halogen. Index m in $R^3$ is preferably 2. Index n is preferably 2.

$R^3$ groups stand preferably in positions 3 and 5.

In another embodiment $R^3$ is preferably halogen, CN, $C_1$-$C_4$-haloalkyl, $C_1$-$C_4$-haloalkoxy, $C_3$-$C_4$-cycloalkyl, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl, or $S(O)_m$—$R^{14}$, wherein $R^{14}$ is phenyl, which is partially substituted with $R^{3a}$.

In another embodiment of formula I compounds $R^3$ is halogen, CN, $NO_2$, $C_1$-$C_4$-alkyl, $C_3$-$C_6$-cycloalkyl, $C_1$-$C_6$-haloalkyl, $C_1$-$C_6$-halocycloalkyl, $OR^{14}$, $S(O)_m$—$R^{14}$; wherein rings are unsubstituted or substituted with $R^{11}$.

$R^4$ is preferably $C_1$-$C_4$-alkyl, $C_1$-$C_4$-haloalkyl, $C_1$-$C_4$-alkoxy-$C_1$-$C_4$-alkyl, $CH_2C(O)NH$—$C_1$-$C_6$-alkyl, $S(O)_m$—$C_1$-$C_4$-alkyl, $C_3$-$C_6$-cycloalkyl, $C_1$-$C_4$-alkyl-$C_3$-$C_6$-cycloalkyl, or phenyl unsubstituted or substituted with one or more groups $R^3$.

In another embodiment $R^4$ is preferably $C_1$-$C_4$-alkyl, $C_1$-$C_4$-haloalkyl, $C_1$-$C_4$-alkoxy-$C_1$-$C_4$-alkyl, $CH_2C(O)NH$-$C_1$-$C_6$-alkyl, $C_3$-$C_6$-cycloalkyl, $C_1$-$C_4$-alkyl-$C_3$-$C_6$-cycloalkyl, or phenyl or 5- or 6-membered heteroaryl which (hetero)aryl groups are unsubstituted or substituted with one or more groups $R^3$, wherein $R^3$ is preferably halogen, CN, or $C_1$-$C_3$-alkoxy.

$R^5$ is preferably H or $C_1$-$C_4$-alkyl, particularly H.

In particular with a view to their use, preference is given to the compounds of formula I compiled in the tables below, which compounds correspond to formulae I.1a*, I.1b*, I.1c*, I.1d*, I.2a*, I.2b*, I.2c*, and I.2d*. Each of the groups mentioned for a substituent in the tables is furthermore per se, independently of the combination in which it is mentioned, a particularly preferred aspect of the substituent in question.

I.1a*

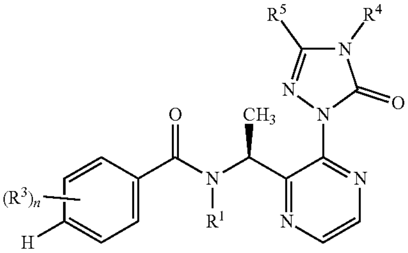

I.1b*

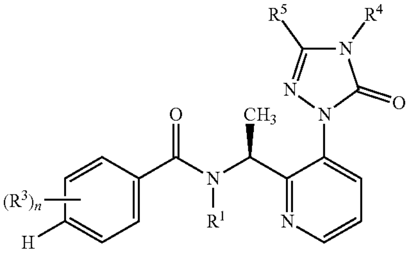

-continued

I.1c*

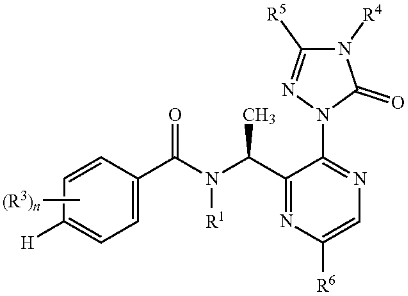

I.1d*

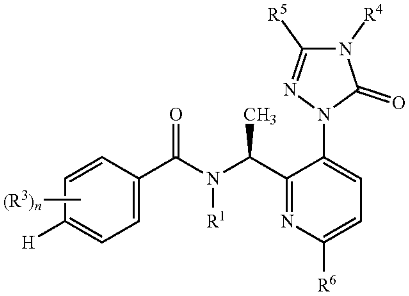

I.2a*

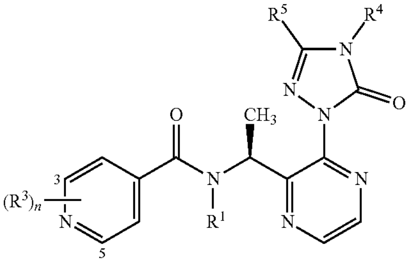

I.2b*

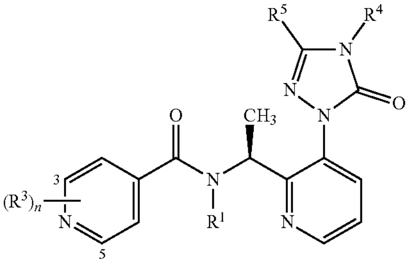

I.2c*

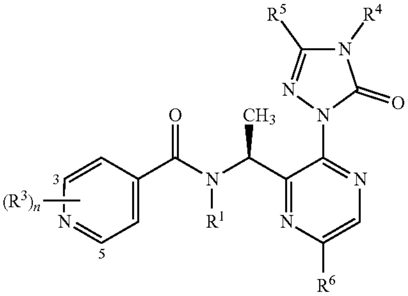

-continued

I.2d*

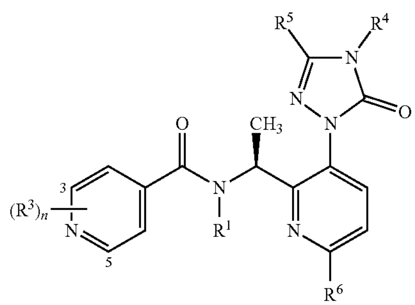

Table 1

Compounds of formula I.1a* in which $R^4$ is $CH_2CF_3$, and the combination of $R^1$, $(R^3)_n$ and $R^5$ for a compound corresponds in each case to one row of Table A Table 2

Compounds of formula I.1a* in which $R^4$ is $CH_3$, and the combination of $R^1$, $(R^3)_n$ and $R^5$ for a compound corresponds in each case to one row of Table A Table 3

Compounds of formula I.1a* in which $R^4$ is $C_2H_5$, and the combination of $R^1$, $(R^3)_n$ and $R^5$ for a compound corresponds in each case to one row of Table A Table 4

Compounds of formula I.1a* in which $R^4$ is $CH(CH_3)_2$, and the combination of $R^1$, $(R^3)_n$ and $R^5$ for a compound corresponds in each case to one row of Table A Table 5

Compounds of formula I.1a* in which $R^4$ is $SO_2CH_3$, and the combination of $R^1$, $(R^3)_n$ and $R^5$ for a compound corresponds in each case to one row of Table A Table 6

Compounds of formula I.1a* in which $R^4$ is $C_6H_5$, and the combination of $R^1$, $(R^3)_n$ and $R^5$ for a compound corresponds in each case to one row of Table A Table 7

Compounds of formula I.1a* in which $R^4$ is $CH_2$-(4-$OCH_3$—$C_6H_4$), and the combination of $R^1$, $(R^3)_n$ and $R^5$ for a compound corresponds in each case to one row of Table A Table 8

Compounds of formula I.1a* in which $R^4$ is $CH_2OCH_3$, and the combination of $R^1$, $(R^3)_n$ and $R^5$ for a compound corresponds in each case to one row of Table A Table 9

Compounds of formula I.1a* in which $R^4$ is $CH_2C(=O)NHCH_3$, and the combination of $R^1$, $(R^3)_n$ and $R^5$ for a compound corresponds in each case to one row of Table A Table 10

Compounds of formula I.1a* in which $R^4$ is $C(=O)OCH_3$, and the combination of $R^1$, $(R^3)_n$ and $R^5$ for a compound corresponds in each case to one row of Table A Table 11

Compounds of formula I.1a* in which $R^4$ is $cC_3H_5$, and the combination of $R^1$, $(R^3)_n$ and $R^5$ for a compound corresponds in each case to one row of Table A Table 12

Compounds of formula I.1a* in which $R^4$ is $CH_2$-$cC_3H_5$, and the combination of $R^1$, $(R^3)_n$ and $R^5$ for a compound corresponds in each case to one row of Table A Table 13

Compounds of formula I.1b* in which $R^4$ is $CH_2CF_3$, and the combination of $R^1$, $(R^3)_n$ and $R^5$ for a compound corresponds in each case to one row of Table A Table 14

Compounds of formula I.1b* in which $R^4$ is $CH_3$, and the combination of $R^1$, $(R^3)_n$ and $R^5$ for a compound corresponds in each case to one row of Table A Table 15

Compounds of formula I.1b* in which $R^4$ is $C_2H_5$, and the combination of $R^1$, $(R^3)_n$ and $R^5$ for a compound corresponds in each case to one row of Table A Table 16

Compounds of formula I.1b* in which $R^4$ is $CH(CH_3)_2$, and the combination of $R^1$, $(R^3)_n$ and $R^5$ for a compound corresponds in each case to one row of Table A Table 17

Compounds of formula I.1b* in which $R^4$ is $SO_2CH_3$, and the combination of $R^1$, $(R^3)_n$ and $R^5$ for a compound corresponds in each case to one row of Table A Table 18

Compounds of formula I.1b* in which $R^4$ is $C_6H_5$, and the combination of $R^1$, $(R^3)_n$ and $R^5$ for a compound corresponds in each case to one row of Table A Table 19

Compounds of formula I.1b* in which $R^4$ is $CH_2$-(4-$OCH_3$—$C_6H_4$), and the combination of $R^1$, $(R^3)_n$ and $R^5$ for a compound corresponds in each case to one row of Table A Table 20

Compounds of formula I.1b* in which $R^4$ is $CH_2OCH_3$, and the combination of $R^1$, $(R^3)_n$ and $R^5$ for a compound corresponds in each case to one row of Table A Table 21

Compounds of formula I.1b* in which $R^4$ is $CH_2C(=O)NHCH_3$, and the combination of $R^1$, $(R^3)_n$ and $R^5$ for a compound corresponds in each case to one row of Table A Table 22

Compounds of formula I.1b* in which $R^4$ is $C(=O)OCH_3$, and the combination of $R^1$, $(R^3)_n$ and $R^5$ for a compound corresponds in each case to one row of Table A Table 23

Compounds of formula I.1b* in which $R^4$ is $cC_3H_5$, and the combination of $R^1$, $(R^3)_n$ and $R^5$ for a compound corresponds in each case to one row of Table A Table 24

Compounds of formula I.1b* in which $R^4$ is $CH_2$-$cC_3H_5$, and the combination of $R^1$, $(R^3)_n$ and $R^5$ for a compound corresponds in each case to one row of Table A Table 25

Compounds of formula I.1c* in which $R^4$ is $CH_2CF_3$, $R^6$ is Cl, and the combination of $R^1$, $(R^3)_n$ and $R^5$ for a compound corresponds in each case to one row of Table A Table 26

Compounds of formula I.1c* in which $R^4$ is $CH_3$, $R^6$ is Cl, and the combination of $R^1$, $(R^3)_n$ and $R^5$ for a compound corresponds in each case to one row of Table A Table 27

Compounds of formula I.1c* in which $R^4$ is $C_2H_5$, $R^6$ is Cl, and the combination of $R^1$, $(R^3)_n$ and $R^5$ for a compound corresponds in each case to one row of Table A Table 28

Compounds of formula I.1c* in which $R^4$ is $CH(CH_3)_2$, $R^6$ is Cl, and the combination of $R^1$, $(R^3)_n$ and $R^5$ for a compound corresponds in each case to one row of Table A Table 29

Compounds of formula I.1c* in which $R^4$ is $SO_2CH_3$, $R^6$ is Cl, and the combination of $R^1$, $(R^3)_n$ and $R^5$ for a compound corresponds in each case to one row of Table A Table 30

Compounds of formula I.1c* in which $R^4$ is $C_6H_5$, and $R^6$ is Cl, the combination of $R^1$, $(R^3)_n$ and $R^5$ for a compound corresponds in each case to one row of Table A Table 31

Compounds of formula I.1c* in which $R^4$ is $CH_2$-(4-$OCH_3$—$C_6H_4$), $R^6$ is Cl, and the combination of $R^1$, $(R^3)_n$ and $R^5$ for a compound corresponds in each case to one row of Table A Table 32

Compounds of formula I.1c* in which $R^4$ is $CH_2OCH_3$, $R^6$ is Cl, and the combination of $R^1$, $(R^3)_n$ and $R^5$ for a compound corresponds in each case to one row of Table A Table 33

Compounds of formula I.1c* in which $R^4$ is $CH_2C(=O)NHCH_3$, $R^5$ is Cl, and the combination of $R^1$, $(R^3)_n$ and $R^5$ for a compound corresponds in each case to one row of Table A Table 34

Compounds of formula I.1c* in which $R^4$ is $C(=O)OCH_3$, $R^6$ is Cl, and the combination of $R^1$, $(R^3)_n$ and $R^5$ for a compound corresponds in each case to one row of Table A Table 35

Compounds of formula I.1c* in which $R^4$ is $cC_3H_5$, $R^6$ is Cl, and the combination of $R^1$, $(R^3)_n$ and $R^5$ for a compound corresponds in each case to one row of Table A Table 36

Compounds of formula I.1c* in which $R^4$ is $CH_2$-$cC_3H_5$, $R^6$ is Cl, and the combination of $R^1$, $(R^3)_n$ and $R^5$ for a compound corresponds in each case to one row of Table A Table 37

Compounds of formula I.1c* in which $R^4$ is $CH_2CF_3$, $R^6$ is $CH_3$, and the combination of $R^1$, $(R^3)_n$ and $R^5$ for a compound corresponds in each case to one row of Table A Table 38

Compounds of formula I.1c* in which $R^4$ is $CH_3$, $R^6$ is $CH_3$, and the combination of $R^1$, $(R^3)_n$ and $R^5$ for a compound corresponds in each case to one row of Table A Table 39

Compounds of formula I.1c* in which $R^4$ is $C_2H_5$, $R^6$ is $CH_3$, and the combination of $R^1$, $(R^3)_n$ and $R^5$ for a compound corresponds in each case to one row of Table A Table 40

Compounds of formula I.1c* in which $R^4$ is $CH(CH_3)_2$, $R^6$ is $CH_3$, and the combination of $R^1$, $(R^3)_n$ and $R^5$ for a compound corresponds in each case to one row of Table A Table 41

Compounds of formula I.1c* in which $R^4$ is $SO_2CH_3$, $R^6$ is $CH_3$, and the combination of $R^1$, $(R^3)_n$ and $R^5$ for a compound corresponds in each case to one row of Table A Table 42

Compounds of formula I.1c* in which $R^4$ is $C_6H_5$, and $R^6$ is $CH_3$, the combination of $R^1$, $(R^3)_n$ and $R^5$ for a compound corresponds in each case to one row of Table A Table 43

Compounds of formula I.1c* in which $R^4$ is $CH_2$-(4-$OCH_3$—$C_6H_4$), $R^6$ is $CH_3$, and the combination of $R^1$, $(R^3)_n$ and $R^5$ for a compound corresponds in each case to one row of Table A Table 44

Compounds of formula I.1c* in which $R^4$ is $CH_2OCH_3$, $R^6$ is $CH_3$, and the combination of $R^1$, $(R^3)_n$ and $R^5$ for a compound corresponds in each case to one row of Table A Table 45

Compounds of formula I.1c* in which $R^4$ is $CH_2C(=O)NHCH_3$, $R^5$ is $CH_3$, and the combination of $R^1$, $(R^3)_n$ and $R^5$ for a compound corresponds in each case to one row of Table A Table 46

Compounds of formula I.1c* in which $R^4$ is $C(=O)OCH_3$, $R^6$ is $CH_3$, and the combination of $R^1$, $(R^3)_n$ and $R^5$ for a compound corresponds in each case to one row of Table A Table 47

Compounds of formula I.1c* in which $R^4$ is $cC_3H_5$, $R^6$ is $CH_3$, and the combination of $R^1$, $(R^3)_n$ and $R^5$ for a compound corresponds in each case to one row of Table A Table 48

Compounds of formula I.1c* in which $R^4$ is $CH_2$-$cC_3H_5$, $R^6$ is $CH_3$, and the combination of $R^1$, $(R^3)_n$ and $R^5$ for a compound corresponds in each case to one row of Table A Table 49

Compounds of formula I.1d* in which $R^4$ is $CH_2CF_3$, $R^6$ is Cl, and the combination of $R^1$, $(R^3)_n$ and $R^5$ for a compound corresponds in each case to one row of Table A Table 50

Compounds of formula I.1d* in which $R^4$ is $CH_3$, $R^6$ is Cl, and the combination of $R^1$, $(R^3)_n$ and $R^5$ for a compound corresponds in each case to one row of Table A Table 51

Compounds of formula I.1d* in which $R^4$ is $C_2H_5$, $R^6$ is Cl, and the combination of $R^1$, $(R^3)_n$ and $R^5$ for a compound corresponds in each case to one row of Table A Table 52

Compounds of formula I.1d* in which $R^4$ is $CH(CH_3)_2$, $R^6$ is Cl, and the combination of $R^1$, $(R^3)_n$ and $R^5$ for a compound corresponds in each case to one row of Table A Table 53

Compounds of formula I.1d* in which $R^4$ is $SO_2CH_3$, $R^6$ is Cl, and the combination of $R^1$, $(R^3)_n$ and $R^5$ for a compound corresponds in each case to one row of Table A Table 54

Compounds of formula I.1d* in which $R^4$ is $C_6H_5$, $R^6$ is Cl, and the combination of $R^1$, $(R^3)_n$ and $R^5$ for a compound corresponds in each case to one row of Table A Table 55

Compounds of formula I.1d* in which $R^4$ is $CH_2$-(4-$OCH_3$—$C_6H_4$), $R^6$ is Cl, and the combination of $R^1$, $(R^3)_n$ and $R^5$ for a compound corresponds in each case to one row of Table A Table 56

Compounds of formula I.1d* in which $R^4$ is $CH_2OCH_3$, $R^6$ is Cl, and the combination of $R^1$, $(R^3)_n$ and $R^5$ for a compound corresponds in each case to one row of Table A Table 57

Compounds of formula I.1d* in which $R^4$ is $CH_2C(=O)NHCH_3$, $R^6$ is Cl, and the combination of $R^1$, $(R^3)_n$ and $R^5$ for a compound corresponds in each case to one row of Table A Table 58

Compounds of formula I.1d* in which $R^4$ is $C(=O)OCH_3$, $R^6$ is Cl, and the combination of $R^1$, $(R^3)_n$ and $R^5$ for a compound corresponds in each case to one row of Table A Table 59

Compounds of formula I.1d* in which $R^4$ is $cC_3H_5$, $R^6$ is Cl, and the combination of $R^1$, $(R^3)_n$ and $R^5$ for a compound corresponds in each case to one row of Table A Table 60

Compounds of formula I.1d* in which $R^4$ is $CH_2$-$cC_3H_5$, $R^6$ is Cl, and the combination of $R^1$, $(R^3)_n$ and $R^5$ for a compound corresponds in each case to one row of Table A Table 61

Compounds of formula I.1d* in which $R^4$ is $CH_2CF_3$, $R^6$ is $CH_3$, and the combination of $R^1$, $(R^3)_n$ and $R^5$ for a compound corresponds in each case to one row of Table A Table 62

Compounds of formula I.1d* in which $R^4$ is $CH_3$, $R^6$ is $CH_3$, and the combination of $R^1$, $(R^3)_n$ and $R^5$ for a compound corresponds in each case to one row of Table A Table 63

Compounds of formula I.1d* in which $R^4$ is $C_2H_5$, $R^6$ is $CH_3$, and the combination of $R^1$, $(R^3)_n$ and $R^5$ for a compound corresponds in each case to one row of Table A Table 64

Compounds of formula I.1d* in which $R^4$ is $CH(CH_3)_2$, $R^6$ is $CH_3$, and the combination of $R^1$, $(R^3)_n$ and $R^5$ for a compound corresponds in each case to one row of Table A Table 65

Compounds of formula I.1d* in which $R^4$ is $SO_2CH_3$, $R^6$ is $CH_3$, and the combination of $R^1$, $(R^3)_n$ and $R^5$ for a compound corresponds in each case to one row of Table A Table 66

Compounds of formula I.1d* in which $R^4$ is $C_6H_5$, and $R^6$ is $CH_3$, the combination of $R^1$, $(R^3)_n$ and $R^5$ for a compound corresponds in each case to one row of Table A Table 67

Compounds of formula I.1d* in which $R^4$ is $CH_2$-(4-$OCH_3$—$C_6H_4$), $R^6$ is $CH_3$, and the combination of $R^1$, $(R^3)_n$ and $R^5$ for a compound corresponds in each case to one row of Table A Table 68

Compounds of formula I.1d* in which $R^4$ is $CH_2OCH_3$, $R^6$ is $CH_3$, and the combination of $R^1$, $(R^3)_n$ and $R^5$ for a compound corresponds in each case to one row of Table A Table 69

Compounds of formula I.1d* in which $R^4$ is $CH_2C(=O)NHCH_3$, $R^6$ is $CH_3$, and the combination of $R^1$, $(R^3)_n$ and $R^5$ for a compound corresponds in each case to one row of Table A Table 70

Compounds of formula I.1d* in which $R^4$ is $C(=O)OCH_3$, $R^6$ is $CH_3$, and the combination of $R^1$, $(R^3)_n$ and $R^5$ for a compound corresponds in each case to one row of Table A Table 71

Compounds of formula I.1d* in which $R^4$ is $cC_3H_5$, $R^6$ is $CH_3$, and the combination of $R^1$, $(R^3)_n$ and $R^5$ for a compound corresponds in each case to one row of Table A Table 72

Compounds of formula I.1d* in which $R^4$ is $CH_2$-$cC_3H_5$, $R^6$ is $CH_3$, and the combination of $R^1$, $(R^3)_n$ and $R^5$ for a compound corresponds in each case to one row of Table A Table 73

Compounds of formula I.2a* in which $R^4$ is $CH_2CF_3$, and the combination of $R^1$, $(R^3)_n$ and $R^5$ for a compound corresponds in each case to one row of Table A Table 74

Compounds of formula I.2a* in which $R^4$ is $CH_3$, and the combination of $R^1$, $(R^3)_n$ and $R^5$ for a compound corresponds in each case to one row of Table A Table 75

Compounds of formula I.2a* in which $R^4$ is $C_2H_5$, and the combination of $R^1$, $(R^3)_n$ and $R^5$ for a compound corresponds in each case to one row of Table A Table 76

Compounds of formula I.2a* in which $R^4$ is $CH(CH_3)_2$, and the combination of $R^1$, $(R^3)_n$ and $R^5$ for a compound corresponds in each case to one row of Table A Table 77

Compounds of formula I.2a* in which $R^4$ is $SO_2CH_3$, and the combination of $R^1$, $(R^3)_n$ and $R^5$ for a compound corresponds in each case to one row of Table A Table 78

Compounds of formula I.2a* in which $R^4$ is $C_6H_5$, and the combination of $R^1$, $(R^3)_n$ and $R^5$ for a compound corresponds in each case to one row of Table A Table 79

Compounds of formula I.2a* in which $R^4$ is $CH_2$-(4-$OCH_3$—$C_6H_4$), and the combination of $R^1$, $(R^3)_n$ and $R^5$ for a compound corresponds in each case to one row of Table A Table 80

Compounds of formula I.2a* in which $R^4$ is $CH_2OCH_3$, and the combination of $R^1$, $(R^3)_n$ and $R^5$ for a compound corresponds in each case to one row of Table A Table 81

Compounds of formula I.2a* in which $R^4$ is $CH_2C(=O)NHCH_3$, and the combination of $R^1$, $(R^3)_n$ and $R^5$ for a compound corresponds in each case to one row of Table A Table 82

Compounds of formula I.2a* in which $R^4$ is $C(=O)OCH_3$, and the combination of $R^1$, $(R^3)_n$ and $R^5$ for a compound corresponds in each case to one row of Table A Table 83

Compounds of formula I.2a* in which $R^4$ is $cC_3H_5$, and the combination of $R^1$, $(R^3)_n$ and $R^5$ for a compound corresponds in each case to one row of Table A Table 84

Compounds of formula I.2a* in which $R^4$ is $CH_2$-$cC_3H_5$, and the combination of $R^1$, $(R^3)_n$ and $R^5$ for a compound corresponds in each case to one row of Table A Table 85

Compounds of formula I.2b* in which $R^4$ is $CH_2CF_3$, and the combination of $R^1$, $(R^3)_n$ and $R^5$ for a compound corresponds in each case to one row of Table A Table 86

Compounds of formula I.2b* in which $R^4$ is $CH_3$, and the combination of $R^1$, $(R^3)_n$ and $R^5$ for a compound corresponds in each case to one row of Table A Table 87

Compounds of formula I.2b* in which $R^4$ is $C_2H_5$, and the combination of $R^1$, $(R^3)_n$ and $R^5$ for a compound corresponds in each case to one row of Table A Table 88

Compounds of formula I.2b* in which $R^4$ is $CH(CH_3)_2$, and the combination of $R^1$, $(R^3)_n$ and $R^5$ for a compound corresponds in each case to one row of Table A Table 89

Compounds of formula I.2b* in which $R^4$ is $SO_2CH_3$, and the combination of $R^1$, $(R^3)_n$ and $R^5$ for a compound corresponds in each case to one row of Table A Table 90

Compounds of formula I.2b* in which $R^4$ is $C_6H_5$, and the combination of $R^1$, $(R^3)_n$ and $R^5$ for a compound corresponds in each case to one row of Table A Table 91

Compounds of formula I.2b* in which $R^4$ is $CH_2$-(4-$OCH_3$—$C_6H_4$), and the combination of $R^1$, $(R^3)_n$ and $R^5$ for a compound corresponds in each case to one row of Table A Table 92

Compounds of formula I.2b* in which $R^4$ is $CH_2OCH_3$, and the combination of $R^1$, $(R^3)_n$ and $R^5$ for a compound corresponds in each case to one row of Table A Table 93

Compounds of formula I.2b* in which $R^4$ is $CH_2C(=O)NHCH_3$, and the combination of $R^1$, $(R^3)_n$ and $R^5$ for a compound corresponds in each case to one row of Table A Table 94

Compounds of formula I.2b* in which $R^4$ is C(=O)$OCH_3$, and the combination of $R^1$, $(R^3)_n$ and $R^5$ for a compound corresponds in each case to one row of Table A Table 95

Compounds of formula I.2b* in which $R^4$ is $cC_3H_5$, and the combination of $R^1$, $(R^3)_n$ and $R^5$ for a compound corresponds in each case to one row of Table A Table 96

Compounds of formula I.2b* in which $R^4$ is $CH_2$-$cC_3H_5$, and the combination of $R^1$, $(R^3)_n$ and $R^5$ for a compound corresponds in each case to one row of Table A Table 97

Compounds of formula I.2c* in which $R^4$ is $CH_2CF_3$, $R^6$ is Cl, and the combination of $R^1$, $(R^3)_n$ and $R^5$ for a compound corresponds in each case to one row of Table A Table 98

Compounds of formula I.2c* in which $R^4$ is $CH_3$, $R^6$ is Cl, and the combination of $R^1$, $(R^3)_n$ and $R^5$ for a compound corresponds in each case to one row of Table A Table 99

Compounds of formula I.2c* in which $R^4$ is $C_2H_5$, $R^6$ is Cl, and the combination of $R^1$, $(R^3)_n$ and $R^5$ for a compound corresponds in each case to one row of Table A Table 100

Compounds of formula I.2c* in which $R^4$ is $CH(CH_3)_2$, $R^6$ is Cl, and the combination of $R^1$, $(R^3)_n$ and $R^5$ for a compound corresponds in each case to one row of Table A Table 101

Compounds of formula I.2c* in which $R^4$ is $SO_2CH_3$, $R^6$ is Cl, and the combination of $R^1$, $(R^3)_n$ and $R^5$ for a compound corresponds in each case to one row of Table A Table 102

Compounds of formula I.2c* in which $R^4$ is $C_6H_5$, $R^6$ is Cl, and the combination of $R^1$, $(R^3)_n$ and $R^5$ for a compound corresponds in each case to one row of Table A Table 103

Compounds of formula I.2c* in which $R^4$ is $CH_2$-(4-$OCH_3$—$C_6H_4$), $R^6$ is Cl, and the combination of $R^1$, $(R^3)_n$ and $R^5$ for a compound corresponds in each case to one row of Table A Table 104

Compounds of formula I.2c* in which $R^4$ is $CH_2OCH_3$, $R^6$ is Cl, and the combination of $R^1$, $(R^3)_n$ and $R^5$ for a compound corresponds in each case to one row of Table A Table 105

Compounds of formula I.2c* in which $R^4$ is $CH_2C$(=O)$NHCH_3$, $R^5$ is Cl, and the combination of $R^1$, $(R^3)_n$ and $R^5$ for a compound corresponds in each case to one row of Table A Table 106

Compounds of formula I.2c* in which $R^4$ is C(=O)$OCH_3$, $R^6$ is Cl, and the combination of $R^1$, $(R^3)_n$ and $R^5$ for a compound corresponds in each case to one row of Table A Table 107

Compounds of formula I.2c* in which $R^4$ is $cC_3H_5$, $R^6$ is Cl, and the combination of $R^1$, $(R^3)_n$ and $R^5$ for a compound corresponds in each case to one row of Table A Table 108

Compounds of formula I.2c* in which $R^4$ is $CH_2$-$cC_3H_5$, $R^6$ is Cl, and the combination of $R^1$, $(R^3)_n$ and $R^5$ for a compound corresponds in each case to one row of Table A Table 109

Compounds of formula I.2c* in which $R^4$ is $CH_2CF_3$, $R^6$ is $CH_3$, and the combination of $R^1$, $(R^3)_n$ and $R^5$ for a compound corresponds in each case to one row of Table A Table 110

Compounds of formula I.2c* in which $R^4$ is $CH_3$, $R^6$ is $CH_3$, and the combination of $R^1$, $(R^3)_n$ and $R^5$ for a compound corresponds in each case to one row of Table A Table 111

Compounds of formula I.2c* in which $R^4$ is $C_2H_5$, $R^6$ is $CH_3$, and the combination of $R^1$, $(R^3)_n$ and $R^5$ for a compound corresponds in each case to one row of Table A Table 112

Compounds of formula I.2c* in which $R^4$ is $CH(CH_3)_2$, $R^6$ is $CH_3$, and the combination of $R^1$, $(R^3)_n$ and $R^5$ for a compound corresponds in each case to one row of Table A Table 113

Compounds of formula I.2c* in which $R^4$ is $SO_2CH_3$, $R^6$ is $CH_3$, and the combination of $R^1$, $(R^3)_n$ and $R^5$ for a compound corresponds in each case to one row of Table A Table 114

Compounds of formula I.2c* in which $R^4$ is $C_6H_5$, and $R^6$ is $CH_3$, the combination of $R^1$, $(R^3)_n$ and $R^5$ for a compound corresponds in each case to one row of Table A Table 115

Compounds of formula I.2c* in which $R^4$ is $CH_2$-(4-$OCH_3$—$C_6H_4$), $R^6$ is $CH_3$, and the combination of $R^1$, $(R^3)_n$ and $R^5$ for a compound corresponds in each case to one row of Table A Table 116

Compounds of formula I.2c* in which $R^4$ is $CH_2OCH_3$, $R^6$ is $CH_3$, and the combination of $R^1$, $(R^3)_n$ and $R^5$ for a compound corresponds in each case to one row of Table A Table 117

Compounds of formula I.2c* in which $R^4$ is $CH_2C$(=O)$NHCH_3$, $R^5$ is $CH_3$, and the combination of $R^1$, $(R^3)_n$ and $R^5$ for a compound corresponds in each case to one row of Table A Table 118

Compounds of formula I.2c* in which $R^4$ is C(=O)$OCH_3$, $R^6$ is $CH_3$, and the combination of $R^1$, $(R^3)_n$ and $R^5$ for a compound corresponds in each case to one row of Table A Table 119

Compounds of formula I.2c* in which $R^4$ is $cC_3H_5$, $R^6$ is $CH_3$, and the combination of $R^1$, $(R^3)_n$ and $R^5$ for a compound corresponds in each case to one row of Table A Table 120

Compounds of formula I.2c* in which $R^4$ is $CH_2$-$cC_3H_5$, $R^6$ is $CH_3$, and the combination of $R^1$, $(R^3)_n$ and $R^5$ for a compound corresponds in each case to one row of Table A Table 121

Compounds of formula I.2d* in which $R^4$ is $CH_2CF_3$, $R^6$ is Cl, and the combination of $R^1$, $(R^3)_n$ and $R^5$ for a compound corresponds in each case to one row of Table A Table 122

Compounds of formula I.2d* in which $R^4$ is $CH_3$, $R^6$ is Cl, and the combination of $R^1$, $(R^3)_n$ and $R^5$ for a compound corresponds in each case to one row of Table A Table 123

Compounds of formula I.2d* in which $R^4$ is $C_2H_5$, $R^6$ is Cl, and the combination of $R^1$, $(R^3)_n$ and $R^5$ for a compound corresponds in each case to one row of Table A Table 124

Compounds of formula I.2d* in which $R^4$ is $CH(CH_3)_2$, $R^6$ is Cl, and the combination of $R^1$, $(R^3)_n$ and $R^5$ for a compound corresponds in each case to one row of Table A Table 125

Compounds of formula I.2d* in which $R^4$ is $SO_2CH_3$, $R^6$ is Cl, and the combination of $R^1$, $(R^3)_n$ and $R^5$ for a compound corresponds in each case to one row of Table A Table 126

Compounds of formula I.2d* in which $R^4$ is $C_6H_5$, $R^6$ is Cl, and the combination of $R^1$, $(R^3)_n$ and $R^5$ for a compound corresponds in each case to one row of Table A Table 127

Compounds of formula I.2d* in which $R^4$ is $CH_2$-(4-$OCH_3$—$C_6H_4$), $R^6$ is Cl, and the combination of $R^1$, $(R^3)_n$ and $R^5$ for a compound corresponds in each case to one row of Table A Table 128

Compounds of formula I.2d* in which $R^4$ is $CH_2OCH_3$, $R^6$ is Cl, and the combination of $R^1$, $(R^3)_n$ and $R^5$ for a compound corresponds in each case to one row of Table A Table 129

Compounds of formula I.2d* in which $R^4$ is $CH_2C({=}O)NHCH_3$, $R^6$ is Cl, and the combination of $R^1$, $(R^3)_n$ and $R^5$ for a compound corresponds in each case to one row of Table A Table 130

Compounds of formula I.2d* in which $R^4$ is $C({=}O)OCH_3$, $R^6$ is Cl, and the combination of $R^1$, $(R^3)_n$ and $R^5$ for a compound corresponds in each case to one row of Table A Table 131

Compounds of formula I.2d* in which $R^4$ is $cC_3H_5$, $R^6$ is Cl, and the combination of $R^1$, $(R^3)_n$ and $R^5$ for a compound corresponds in each case to one row of Table A Table 132

Compounds of formula I.2d* in which $R^4$ is $CH_2$-$cC_3H_5$, $R^6$ is Cl, and the combination of $R^1$, $(R^3)_n$ and $R^5$ for a compound corresponds in each case to one row of Table A Table 133

Compounds of formula I.2d* in which $R^4$ is $CH_2CF_3$, $R^6$ is $CH_3$, and the combination of $R^1$, $(R^3)_n$ and $R^5$ for a compound corresponds in each case to one row of Table A Table 134

Compounds of formula I.2d* in which $R^4$ is $CH_3$, $R^6$ is $CH_3$, and the combination of $R^1$, $(R^3)_n$ and $R^5$ for a compound corresponds in each case to one row of Table A Table 135

Compounds of formula I.2d* in which $R^4$ is $C_2H_5$, $R^6$ is $CH_3$, and the combination of $R^1$, $(R^3)_n$ and $R^5$ for a compound corresponds in each case to one row of Table A Table 136

Compounds of formula I.2d* in which $R^4$ is $CH(CH_3)_2$, $R^6$ is $CH_3$, and the combination of $R^1$, $(R^3)_n$ and $R^5$ for a compound corresponds in each case to one row of Table A Table 137

Compounds of formula I.2d* in which $R^4$ is $SO_2CH_3$, $R^6$ is $CH_3$, and the combination of $R^1$, $(R^3)_n$ and $R^5$ for a compound corresponds in each case to one row of Table A Table 138

Compounds of formula I.2d* in which $R^4$ is $C_6H_5$, and $R^6$ is $CH_3$, the combination of $R^1$, $(R^3)_n$ and $R^5$ for a compound corresponds in each case to one row of Table A Table 139

Compounds of formula I.2d* in which $R^4$ is $CH_2$-(4-$OCH_3$—$C_6H_4$), $R^6$ is $CH_3$, and the combination of $R^1$, $(R^3)_n$ and $R^5$ for a compound corresponds in each case to one row of Table A Table 140

Compounds of formula I.2d* in which $R^4$ is $CH_2OCH_3$, $R^6$ is $CH_3$, and the combination of $R^1$, $(R^3)_n$ and $R^5$ for a compound corresponds in each case to one row of Table A Table 141

Compounds of formula I.2d* in which $R^4$ is $CH_2C({=}O)NHCH_3$, $R^6$ is $CH_3$, and the combination of $R^1$, $(R^3)_n$ and $R^5$ for a compound corresponds in each case to one row of Table A Table 142

Compounds of formula I.2d* in which $R^4$ is $C({=}O)OCH_3$, $R^6$ is $CH_3$, and the combination of $R^1$, $(R^3)_n$ and $R^5$ for a compound corresponds in each case to one row of Table A Table 143

Compounds of formula I.2d* in which $R^4$ is $cC_3H_5$, $R^6$ is $CH_3$, and the combination of $R^1$, $(R^3)_n$ and $R^5$ for a compound corresponds in each case to one row of Table A Table 144

Compounds of formula I.2d* in which $R^4$ is $CH_2$-$cC_3H_5$, $R^6$ is $CH_3$, and the combination of $R^1$, $(R^3)_n$ and $R^5$ for a compound corresponds in each case to one row of Table A

TABLE A

| No. | $R^1$ | $(R^3)_n$ | $R^5$ |
|---|---|---|---|
| A-1 | H | 3,5-$F_2$ | H |
| A-2 | H | 3,5-$Cl_2$ | H |
| A-3 | H | 3,5-$Br_2$ | H |
| A-4 | H | 3,5-$I_2$ | H |
| A-5 | H | 3,5-$(CF_3)_2$ | H |
| A-6 | H | 3-Cl, 5-F | H |
| A-7 | H | 3-Cl, 5-Br | H |
| A-8 | H | 3-Cl, 5-I | H |
| A-9 | H | 3-F, 5-CN | H |
| A-10 | H | 3-Cl, 5-CN | H |
| A-11 | H | 3-$CF_3$, 5-CN | H |
| A-12 | H | 3-F, 5-$CF_3$ | H |
| A-13 | H | 3-Cl, 5-$CF_3$ | H |
| A-14 | H | 3-Br, 5-$CF_3$ | H |
| A-15 | H | 3-I, 5-$CF_3$ | H |
| A-16 | H | 3-Cl, 5-$SO_2CH_3$ | H |
| A-17 | H | 3-Cl, 5-$SO_2CF_3$ | H |
| A-18 | H | 3-Cl, 5-$cC_3H_5$ | H |
| A-19 | H | 3-Cl, 5-[2,2-$Cl_2$-$cC_3H_3$] | H |
| A-20 | H | 3-Cl, 5-$OCF_3$ | H |
| A-21 | H | 3-Br, 5-$OCF_3$ | H |
| A-22 | H | 3-F, 5-$cC_3H_5$ | H |
| A-23 | H | 3-Cl, 5-$CH_2CN$ | H |
| A-24 | H | 3-Cl, 5-$C(CH_3)_2CN$ | H |
| A-25 | H | 3-$CF_3$, 5-$CH_2CN$ | H |
| A-26 | H | 3-$CF_3$, 5-$C(CH_3)_2CN$ | H |
| A-27 | H | 3-$CF_3$, 5-$SO_2CH_3$ | H |
| A-28 | H | 3-$CF_3$, 5-$SO_2CF_3$ | H |
| A-29 | H | 3-$CF_3$, 5-$OCF_3$ | H |
| A-30 | H | 3-$CF_3$, 5-$cC_3H_5$ | H |
| A-31 | H | 3-Cl, 5-[(1-CN)$cC_3H_4$] | H |
| A-32 | H | 3-$CF_3$, 5-[(1-CN)$cC_3H_4$] | H |
| A-33 | H | 3-$CF_3$, 5-[(2,2-$Cl_2$)-$cC_3H_3$] | H |
| A-34 | H | 3-$OCF_3$, 5-$cC_3H_5$ | H |
| A-35 | H | 3,5-$SO_2CH_3$ | H |
| A-36 | H | 3,5-$SO_2CF_3$ | H |
| A-37 | H | 3-Cl, 5-$OC_6H_5$ | H |
| A-38 | H | 3-$CF_3$, 5-$OC_6H_5$ | H |
| A-39 | H | 3-$CF_3$, 5-[O-(4-Cl—$C_6H_4$)] | H |
| A-40 | $CH_2$-$cC_3H_5$ | 3,5-$F_2$ | H |
| A-41 | $CH_2$-$cC_3H_5$ | 3,5-$Cl_2$ | H |
| A-42 | $CH_2$-$cC_3H_5$ | 3,5-$Br_2$ | H |
| A-43 | $CH_2$-$cC_3H_5$ | 3,5-$I_2$ | H |
| A-44 | $CH_2$-$cC_3H_5$ | 3,5-$(CF_3)_2$ | H |
| A-45 | $CH_2$-$cC_3H_5$ | 3-Cl, 5-F | H |
| A-46 | $CH_2$-$cC_3H_5$ | 3-Cl, 5-Br | H |
| A-47 | $CH_2$-$cC_3H_5$ | 3-Cl, 5-I | H |
| A-48 | $CH_2$-$cC_3H_5$ | 3-F, 5-CN | H |
| A-49 | $CH_2$-$cC_3H_5$ | 3-Cl, 5-CN | H |
| A-50 | $CH_2$-$cC_3H_5$ | 3-$CF_3$, 5-CN | H |
| A-51 | $CH_2$-$cC_3H_5$ | 3-F, 5-$CF_3$ | H |
| A-52 | $CH_2$-$cC_3H_5$ | 3-Cl, 5-$CF_3$ | H |
| A-53 | $CH_2$-$cC_3H_5$ | 3-Br, 5-$CF_3$ | H |
| A-54 | $CH_2$-$cC_3H_5$ | 3-I, 5-$CF_3$ | H |
| A-55 | $CH_2$-$cC_3H_5$ | 3-Cl, 5-$SO_2CH_3$ | H |

TABLE A-continued

| No. | $R^1$ | $(R^3)_n$ | $R^5$ |
|---|---|---|---|
| A-56 | $CH_2$-$cC_3H_5$ | 3-Cl, 5-$SO_2CF_3$ | H |
| A-57 | $CH_2$-$cC_3H_5$ | 3-Cl, 5-$cC_3H_5$ | H |
| A-58 | $CH_2$-$cC_3H_5$ | 3-Cl, 5-[2,2-$Cl_2$-$cC_3H_3$] | H |
| A-59 | $CH_2$-$cC_3H_5$ | 3-Cl, 5-$OCF_3$ | H |
| A-60 | $CH_2$-$cC_3H_5$ | 3-Br, 5-$OCF_3$ | H |
| A-61 | $CH_2$-$cC_3H_5$ | 3-F, 5-$cC_3H_5$ | H |
| A-62 | $CH_2$-$cC_3H_5$ | 3-Cl, 5-$CH_2CN$ | H |
| A-63 | $CH_2$-$cC_3H_5$ | 3-Cl, 5-$C(CH_3)_2CN$ | H |
| A-64 | $CH_2$-$cC_3H_5$ | 3-$CF_3$, 5-$CH_2CN$ | H |
| A-65 | $CH_2$-$cC_3H_5$ | 3-$CF_3$, 5-$C(CH_3)_2CN$ | H |
| A-66 | $CH_2$-$cC_3H_5$ | 3-$CF_3$, 5-$SO_2CH_3$ | H |
| A-67 | $CH_2$-$cC_3H_5$ | 3-$CF_3$, 5-$SO_2CF_3$ | H |
| A-68 | $CH_2$-$cC_3H_5$ | 3-$CF_3$, 5-$OCF_3$ | H |
| A-69 | $CH_2$-$cC_3H_5$ | 3-$CF_3$, 5-$cC_3H_5$ | H |
| A-70 | $CH_2$-$cC_3H_5$ | 3-Cl, 5-[(1-CN)$cC_3H_4$] | H |
| A-71 | $CH_2$-$cC_3H_5$ | 3-$CF_3$, 5-[(1-CN)$cC_3H_4$] | H |
| A-72 | $CH_2$-$cC_3H_5$ | 3-$CF_3$, 5-[(2,2-$Cl_2$)-$cC_3H_3$] | H |
| A-73 | $CH_2$-$cC_3H_5$ | 3-$OCF_3$, 5-$cC_3H_5$ | H |
| A-74 | $CH_2$-$cC_3H_5$ | 3,5-$SO_2CH_3$ | H |
| A-75 | $CH_2$-$cC_3H_5$ | 3,5-$SO_2CF_3$ | H |
| A-76 | $CH_2$-$cC_3H_5$ | 3-Cl, 5-$OC_6H_5$ | H |
| A-77 | $CH_2$-$cC_3H_5$ | 3-$CF_3$, 5-$OC_6H_5$ | H |
| A-78 | $CH_2$-$cC_3H_5$ | 3-$CF_3$, 5-[O-(4-Cl—$C_6H_4$)] | H |
| A-79 | H | 3,5-$F_2$ | Cl |
| A-80 | H | 3,5-$Cl_2$ | Cl |
| A-81 | H | 3,5-$Br_2$ | Cl |
| A-82 | H | 3,5-$I_2$ | Cl |
| A-83 | H | 3,5-$(CF_3)_2$ | Cl |
| A-84 | H | 3-Cl, 5-F | Cl |
| A-85 | H | 3-Cl, 5-Br | Cl |
| A-86 | H | 3-Cl, 5-I | Cl |
| A-87 | H | 3-F, 5-CN | Cl |
| A-88 | H | 3-Cl, 5-CN | Cl |
| A-89 | H | 3-$CF_3$, 5-CN | Cl |
| A-90 | H | 3-F, 5-$CF_3$ | Cl |
| A-91 | H | 3-Cl, 5-$CF_3$ | Cl |
| A-92 | H | 3-Br, 5-$CF_3$ | Cl |
| A-93 | H | 3-I, 5-$CF_3$ | Cl |
| A-94 | H | 3-Cl, 5-$SO_2CH_3$ | Cl |
| A-95 | H | 3-Cl, 5-$SO_2CF_3$ | Cl |
| A-96 | H | 3-Cl, 5-$cC_3H_5$ | Cl |
| A-97 | H | 3-Cl, 5-[2,2-$Cl_2$-$cC_3H_3$] | Cl |
| A-98 | H | 3-Cl, 5-$OCF_3$ | Cl |
| A-99 | H | 3-Br, 5-$OCF_3$ | Cl |
| A-100 | H | 3-F, 5-$cC_3H_5$ | Cl |
| A-101 | H | 3-Cl, 5-$CH_2CN$ | Cl |
| A-102 | H | 3-Cl, 5-$C(CH_3)_2CN$ | Cl |
| A-103 | H | 3-$CF_3$, 5-$CH_2CN$ | Cl |
| A-104 | H | 3-$CF_3$, 5-$C(CH_3)_2CN$ | Cl |
| A-105 | H | 3-$CF_3$, 5-$SO_2CH_3$ | Cl |
| A-106 | H | 3-$CF_3$, 5-$SO_2CF_3$ | Cl |
| A-107 | H | 3-$CF_3$, 5-$OCF_3$ | Cl |
| A-108 | H | 3-$CF_3$, 5-$cC_3H_5$ | Cl |
| A-109 | H | 3-Cl, 5-[(1-CN)$cC_3H_4$] | Cl |
| A-110 | H | 3-$CF_3$, 5-[(1-CN)$cC_3H_4$] | Cl |
| A-111 | H | 3-$CF_3$, 5-[(2,2-$Cl_2$)-$cC_3H_3$] | Cl |
| A-112 | H | 3-$OCF_3$, 5-$cC_3H_5$ | Cl |
| A-113 | H | 3,5-$SO_2CH_3$ | Cl |
| A-114 | H | 3,5-$SO_2CF_3$ | Cl |
| A-115 | H | 3-Cl, 5-$OC_6H_5$ | Cl |
| A-116 | H | 3-$CF_3$, 5-$OC_6H_5$ | Cl |
| A-117 | H | 3-$CF_3$, 5-[O-(4-Cl—$C_6H_4$)] | Cl |
| A-118 | $CH_2$-$cC_3H_5$ | 3,5-$F_2$ | Cl |
| A-119 | $CH_2$-$cC_3H_5$ | 3,5-$Cl_2$ | Cl |
| A-120 | $CH_2$-$cC_3H_5$ | 3,5-$Br_2$ | Cl |
| A-121 | $CH_2$-$cC_3H_5$ | 3,5-$I_2$ | Cl |
| A-122 | $CH_2$-$cC_3H_5$ | 3,5-$(CF_3)_2$ | Cl |
| A-123 | $CH_2$-$cC_3H_5$ | 3-Cl, 5-F | Cl |
| A-124 | $CH_2$-$cC_3H_5$ | 3-Cl, 5-Br | Cl |
| A-125 | $CH_2$-$cC_3H_5$ | 3-Cl, 5-I | Cl |
| A-126 | $CH_2$-$cC_3H_5$ | 3-F, 5-CN | Cl |
| A-127 | $CH_2$-$cC_3H_5$ | 3-Cl, 5-CN | Cl |
| A-128 | $CH_2$-$cC_3H_5$ | 3-$CF_3$, 5-CN | Cl |
| A-129 | $CH_2$-$cC_3H_5$ | 3-F, 5-$CF_3$ | Cl |
| A-130 | $CH_2$-$cC_3H_5$ | 3-Cl, 5-$CF_3$ | Cl |
| A-131 | $CH_2$-$cC_3H_5$ | 3-Br, 5-$CF_3$ | Cl |
| A-132 | $CH_2$-$cC_3H_5$ | 3-I, 5-$CF_3$ | Cl |
| A-133 | $CH_2$-$cC_3H_5$ | 3-Cl, 5-$SO_2CH_3$ | Cl |

TABLE A-continued

| No. | $R^1$ | $(R^3)_n$ | $R^5$ |
|---|---|---|---|
| A-134 | $CH_2$-$cC_3H_5$ | 3-Cl, 5-$SO_2CF_3$ | Cl |
| A-135 | $CH_2$-$cC_3H_5$ | 3-Cl, 5-$cC_3H_5$ | Cl |
| A-136 | $CH_2$-$cC_3H_5$ | 3-Cl, 5-[2,2-$Cl_2$-$cC_3H_3$] | Cl |
| A-137 | $CH_2$-$cC_3H_5$ | 3-Cl, 5-$OCF_3$ | Cl |
| A-138 | $CH_2$-$cC_3H_5$ | 3-Br, 5-$OCF_3$ | Cl |
| A-139 | $CH_2$-$cC_3H_5$ | 3-F, 5-$cC_3H_5$ | Cl |
| A-140 | $CH_2$-$cC_3H_5$ | 3-Cl, 5-$CH_2CN$ | Cl |
| A-141 | $CH_2$-$cC_3H_5$ | 3-Cl, 5-$C(CH_3)_2CN$ | Cl |
| A-142 | $CH_2$-$cC_3H_5$ | 3-$CF_3$, 5-$CH_2CN$ | Cl |
| A-143 | $CH_2$-$cC_3H_5$ | 3-$CF_3$, 5-$C(CH_3)_2CN$ | Cl |
| A-144 | $CH_2$-$cC_3H_5$ | 3-$CF_3$, 5-$SO_2CH_3$ | Cl |
| A-145 | $CH_2$-$cC_3H_5$ | 3-$CF_3$, 5-$SO_2CF_3$ | Cl |
| A-146 | $CH_2$-$cC_3H_5$ | 3-$CF_3$, 5-$OCF_3$ | Cl |
| A-147 | $CH_2$-$cC_3H_5$ | 3-$CF_3$, 5-$cC_3H_5$ | Cl |
| A-148 | $CH_2$-$cC_3H_5$ | 3-Cl, 5-[(1-CN)$cC_3H_4$] | Cl |
| A-149 | $CH_2$-$cC_3H_5$ | 3-$CF_3$, 5-[(1-CN)$cC_3H_4$] | Cl |
| A-150 | $CH_2$-$cC_3H_5$ | 3-$CF_3$, 5-[(2,2-$Cl_2$)-$cC_3H_3$] | Cl |
| A-151 | $CH_2$-$cC_3H_5$ | 3-$OCF_3$, 5-$cC_3H_5$ | Cl |
| A-152 | $CH_2$-$cC_3H_5$ | 3,5-$SO_2CH_3$ | Cl |
| A-153 | $CH_2$-$cC_3H_5$ | 3,5-$SO_2CF_3$ | Cl |
| A-154 | $CH_2$-$cC_3H_5$ | 3-Cl, 5-$OC_6H_5$ | Cl |
| A-155 | $CH_2$-$cC_3H_5$ | 3-$CF_3$, 5-$OC_6H_5$ | Cl |
| A-156 | $CH_2$-$cC_3H_5$ | 3-$CF_3$, 5-[O-(4-Cl—$C_6H_4$)] | Cl |
| A-157 | H | 3,5-$F_2$ | $CH_3$ |
| A-158 | H | 3,5-$Cl_2$ | $CH_3$ |
| A-159 | H | 3,5-$Br_2$ | $CH_3$ |
| A-160 | H | 3,5-$I_2$ | $CH_3$ |
| A-161 | H | 3,5-$(CF_3)_2$ | $CH_3$ |
| A-162 | H | 3-Cl, 5-F | $CH_3$ |
| A-163 | H | 3-Cl, 5-Br | $CH_3$ |
| A-164 | H | 3-Cl, 5-I | $CH_3$ |
| A-165 | H | 3-F, 5-CN | $CH_3$ |
| A-166 | H | 3-Cl, 5-CN | $CH_3$ |
| A-167 | H | 3-$CF_3$, 5-CN | $CH_3$ |
| A-168 | H | 3-F, 5-$CF_3$ | $CH_3$ |
| A-169 | H | 3-Cl, 5-$CF_3$ | $CH_3$ |
| A-170 | H | 3-Br, 5-$CF_3$ | $CH_3$ |
| A-171 | H | 3-I, 5-$CF_3$ | $CH_3$ |
| A-172 | H | 3-Cl, 5-$SO_2CH_3$ | $CH_3$ |
| A-173 | H | 3-Cl, 5-$SO_2CF_3$ | $CH_3$ |
| A-174 | H | 3-Cl, 5-$cC_3H_5$ | $CH_3$ |
| A-175 | H | 3-Cl, 5-[2,2-$Cl_2$-$cC_3H_3$] | $CH_3$ |
| A-176 | H | 3-Cl, 5-$OCF_3$ | $CH_3$ |
| A-177 | H | 3-Br, 5-$OCF_3$ | $CH_3$ |
| A-178 | H | 3-F, 5-$cC_3H_5$ | $CH_3$ |
| A-179 | H | 3-Cl, 5-$CH_2CN$ | $CH_3$ |
| A-180 | H | 3-Cl, 5-$C(CH_3)_2CN$ | $CH_3$ |
| A-181 | H | 3-$CF_3$, 5-$CH_2CN$ | $CH_3$ |
| A-182 | H | 3-$CF_3$, 5-$C(CH_3)_2CN$ | $CH_3$ |
| A-183 | H | 3-$CF_3$, 5-$SO_2CH_3$ | $CH_3$ |
| A-184 | H | 3-$CF_3$, 5-$SO_2CF_3$ | $CH_3$ |
| A-185 | H | 3-$CF_3$, 5-$OCF_3$ | $CH_3$ |
| A-186 | H | 3-$CF_3$, 5-$cC_3H_5$ | $CH_3$ |
| A-187 | H | 3-Cl, 5-[(1-CN)$cC_3H_4$] | $CH_3$ |
| A-188 | H | 3-$CF_3$, 5-[(1-CN)$cC_3H_4$] | $CH_3$ |
| A-189 | H | 3-$CF_3$, 5-[(2,2-$Cl_2$)-$cC_3H_3$] | $CH_3$ |
| A-190 | H | 3-$OCF_3$, 5-$cC_3H_5$ | $CH_3$ |
| A-191 | H | 3,5-$SO_2CH_3$ | $CH_3$ |
| A-192 | H | 3,5-$SO_2CF_3$ | $CH_3$ |
| A-193 | H | 3-Cl, 5-$OC_6H_5$ | $CH_3$ |
| A-194 | H | 3-$CF_3$, 5-$OC_6H_5$ | $CH_3$ |
| A-195 | H | 3-$CF_3$, 5-[O-(4-Cl—$C_6H_4$)] | $CH_3$ |
| A-196 | $CH_2$-$cC_3H_5$ | 3,5-$F_2$ | $CH_3$ |
| A-197 | $CH_2$-$cC_3H_5$ | 3,5-$Cl_2$ | $CH_3$ |
| A-198 | $CH_2$-$cC_3H_5$ | 3,5-$Br_2$ | $CH_3$ |
| A-199 | $CH_2$-$cC_3H_5$ | 3,5-$I_2$ | $CH_3$ |
| A-200 | $CH_2$-$cC_3H_5$ | 3,5-$(CF_3)_2$ | $CH_3$ |
| A-201 | $CH_2$-$cC_3H_5$ | 3-Cl, 5-F | $CH_3$ |
| A-202 | $CH_2$-$cC_3H_5$ | 3-Cl, 5-Br | $CH_3$ |
| A-203 | $CH_2$-$cC_3H_5$ | 3-Cl, 5-I | $CH_3$ |
| A-204 | $CH_2$-$cC_3H_5$ | 3-F, 5-CN | $CH_3$ |
| A-205 | $CH_2$-$cC_3H_5$ | 3-Cl, 5-CN | $CH_3$ |
| A-206 | $CH_2$-$cC_3H_5$ | 3-$CF_3$, 5-CN | $CH_3$ |
| A-207 | $CH_2$-$cC_3H_5$ | 3-F, 5-$CF_3$ | $CH_3$ |
| A-208 | $CH_2$-$cC_3H_5$ | 3-Cl, 5-$CF_3$ | $CH_3$ |
| A-209 | $CH_2$-$cC_3H_5$ | 3-Br, 5-$CF_3$ | $CH_3$ |
| A-210 | $CH_2$-$cC_3H_5$ | 3-I, 5-$CF_3$ | $CH_3$ |
| A-211 | $CH_2$-$cC_3H_5$ | 3-Cl, 5-$SO_2CH_3$ | $CH_3$ |

TABLE A-continued

| No. | $R^1$ | $(R^3)_n$ | $R^5$ |
|---|---|---|---|
| A-212 | $CH_2$-$cC_3H_5$ | 3-Cl, 5-$SO_2CF_3$ | $CH_3$ |
| A-213 | $CH_2$-$cC_3H_5$ | 3-Cl, 5-$cC_3H_5$ | $CH_3$ |
| A-214 | $CH_2$-$cC_3H_5$ | 3-Cl, 5-[2,2-$Cl_2$-$cC_3H_3$] | $CH_3$ |
| A-215 | $CH_2$-$cC_3H_5$ | 3-Cl, 5-$OCF_3$ | $CH_3$ |
| A-216 | $CH_2$-$cC_3H_5$ | 3-Br, 5-$OCF_3$ | $CH_3$ |
| A-217 | $CH_2$-$cC_3H_5$ | 3-F, 5-$cC_3H_5$ | $CH_3$ |
| A-218 | $CH_2$-$cC_3H_5$ | 3-Cl, 5-$CH_2CN$ | $CH_3$ |
| A-219 | $CH_2$-$cC_3H_5$ | 3-Cl, 5-$C(CH_3)_2CN$ | $CH_3$ |
| A-220 | $CH_2$-$cC_3H_5$ | 3-$CF_3$, 5-$CH_2CN$ | $CH_3$ |
| A-221 | $CH_2$-$cC_3H_5$ | 3-$CF_3$, 5-$C(CH_3)_2CN$ | $CH_3$ |
| A-222 | $CH_2$-$cC_3H_5$ | 3-$CF_3$, 5-$SO_2CH_3$ | $CH_3$ |
| A-223 | $CH_2$-$cC_3H_5$ | 3-$CF_3$, 5-$SO_2CF_3$ | $CH_3$ |
| A-224 | $CH_2$-$cC_3H_5$ | 3-$CF_3$, 5-$OCF_3$ | $CH_3$ |
| A-225 | $CH_2$-$cC_3H_5$ | 3-$CF_3$, 5-$cC_3H_5$ | $CH_3$ |
| A-226 | $CH_2$-$cC_3H_5$ | 3-Cl, 5-[(1-CN)$cC_3H_4$] | $CH_3$ |
| A-227 | $CH_2$-$cC_3H_5$ | 3-$CF_3$, 5-[(1-CN)$cC_3H_4$] | $CH_3$ |
| A-228 | $CH_2$-$cC_3H_5$ | 3-$CF_3$, 5-[(2,2-$Cl_2$)-$cC_3H_3$] | $CH_3$ |
| A-229 | $CH_2$-$cC_3H_5$ | 3-$OCF_3$, 5-$cC_3H_5$ | $CH_3$ |
| A-230 | $CH_2$-$cC_3H_5$ | 3,5-$SO_2CH_3$ | $CH_3$ |
| A-231 | $CH_2$-$cC_3H_5$ | 3,5-$SO_2CF_3$ | $CH_3$ |
| A-232 | $CH_2$-$cC_3H_5$ | 3-Cl, 5-$OC_6H_5$ | $CH_3$ |
| A-233 | $CH_2$-$cC_3H_5$ | 3-$CF_3$, 5-$OC_6H_5$ | $CH_3$ |
| A-234 | $CH_2$-$cC_3H_5$ | 3-$CF_3$, 5-[O-(4-Cl—$C_6H_4$)] | $CH_3$ |
| A-235 | H | 3,5-$F_2$ | $OCH_3$ |
| A-236 | H | 3,5-$Cl_2$ | $OCH_3$ |
| A-237 | H | 3,5-$Br_2$ | $OCH_3$ |
| A-238 | H | 3,5-$I_2$ | $OCH_3$ |
| A-239 | H | 3,5-$(CF_3)_2$ | $OCH_3$ |
| A-240 | H | 3-Cl, 5-F | $OCH_3$ |
| A-241 | H | 3-Cl, 5-Br | $OCH_3$ |
| A-242 | H | 3-Cl, 5-I | $OCH_3$ |
| A-243 | H | 3-F, 5-CN | $OCH_3$ |
| A-244 | H | 3-Cl, 5-CN | $OCH_3$ |
| A-245 | H | 3-$CF_3$, 5-CN | $OCH_3$ |
| A-246 | H | 3-F, 5-$CF_3$ | $OCH_3$ |
| A-247 | H | 3-Cl, 5-$CF_3$ | $OCH_3$ |
| A-248 | H | 3-Br, 5-$CF_3$ | $OCH_3$ |
| A-249 | H | 3-I, 5-$CF_3$ | $OCH_3$ |
| A-250 | H | 3-Cl, 5-$SO_2CH_3$ | $OCH_3$ |
| A-251 | H | 3-Cl, 5-$SO_2CF_3$ | $OCH_3$ |
| A-252 | H | 3-Cl, 5-$cC_3H_5$ | $OCH_3$ |
| A-253 | H | 3-Cl, 5-[2,2-$Cl_2$-$cC_3H_3$] | $OCH_3$ |
| A-254 | H | 3-Cl, 5-$OCF_3$ | $OCH_3$ |
| A-255 | H | 3-Br, 5-$OCF_3$ | $OCH_3$ |
| A-256 | H | 3-F, 5-$cC_3H_5$ | $OCH_3$ |
| A-257 | H | 3-Cl, 5-$CH_2CN$ | $OCH_3$ |
| A-258 | H | 3-Cl, 5-$C(CH_3)_2CN$ | $OCH_3$ |
| A-259 | H | 3-$CF_3$, 5-$CH_2CN$ | $OCH_3$ |
| A-260 | H | 3-$CF_3$, 5-$C(CH_3)_2CN$ | $OCH_3$ |
| A-261 | H | 3-$CF_3$, 5-$SO_2CH_3$ | $OCH_3$ |
| A-262 | H | 3-$CF_3$, 5-$SO_2CF_3$ | $OCH_3$ |
| A-263 | H | 3-$CF_3$, 5-$OCF_3$ | $OCH_3$ |
| A-264 | H | 3-$CF_3$, 5-$cC_3H_5$ | $OCH_3$ |
| A-265 | H | 3-Cl, 5-[(1-CN)$cC_3H_4$] | $OCH_3$ |
| A-266 | H | 3-$CF_3$, 5-[(1-CN)$cC_3H_4$] | $OCH_3$ |
| A-267 | H | 3-$CF_3$, 5-[(2,2-$Cl_2$)-$cC_3H_3$] | $OCH_3$ |
| A-268 | H | 3-$OCF_3$, 5-$cC_3H_5$ | $OCH_3$ |
| A-269 | H | 3,5-$SO_2CH_3$ | $OCH_3$ |
| A-270 | H | 3,5-$SO_2CF_3$ | $OCH_3$ |
| A-271 | H | 3-Cl, 5-$OC_6H_5$ | $OCH_3$ |
| A-272 | H | 3-$CF_3$, 5-$OC_6H_5$ | $OCH_3$ |
| A-273 | H | 3-$CF_3$, 5-[O-(4-Cl—$C_6H_4$)] | $OCH_3$ |
| A-274 | $CH_2$-$cC_3H_5$ | 3,5-$F_2$ | $OCH_3$ |
| A-275 | $CH_2$-$cC_3H_5$ | 3,5-$Cl_2$ | $OCH_3$ |
| A-276 | $CH_2$-$cC_3H_5$ | 3,5-$Br_2$ | $OCH_3$ |
| A-277 | $CH_2$-$cC_3H_5$ | 3,5-$I_2$ | $OCH_3$ |
| A-278 | $CH_2$-$cC_3H_5$ | 3,5-$(CF_3)_2$ | $OCH_3$ |
| A-279 | $CH_2$-$cC_3H_5$ | 3-Cl, 5-F | $OCH_3$ |
| A-280 | $CH_2$-$cC_3H_5$ | 3-Cl, 5-Br | $OCH_3$ |
| A-281 | $CH_2$-$cC_3H_5$ | 3-Cl, 5-I | $OCH_3$ |
| A-282 | $CH_2$-$cC_3H_5$ | 3-F, 5-CN | $OCH_3$ |
| A-283 | $CH_2$-$cC_3H_5$ | 3-Cl, 5-CN | $OCH_3$ |
| A-284 | $CH_2$-$cC_3H_5$ | 3-$CF_3$, 5-CN | $OCH_3$ |
| A-285 | $CH_2$-$cC_3H_5$ | 3-F, 5-$CF_3$ | $OCH_3$ |
| A-286 | $CH_2$-$cC_3H_5$ | 3-Cl, 5-$CF_3$ | $OCH_3$ |
| A-287 | $CH_2$-$cC_3H_5$ | 3-Br, 5-$CF_3$ | $OCH_3$ |
| A-288 | $CH_2$-$cC_3H_5$ | 3-I, 5-$CF_3$ | $OCH_3$ |
| A-289 | $CH_2$-$cC_3H_5$ | 3-Cl, 5-$SO_2CH_3$ | $OCH_3$ |
| A-290 | $CH_2$-$cC_3H_5$ | 3-Cl, 5-$SO_2CF_3$ | $OCH_3$ |
| A-291 | $CH_2$-$cC_3H_5$ | 3-Cl, 5-$cC_3H_5$ | $OCH_3$ |
| A-292 | $CH_2$-$cC_3H_5$ | 3-Cl, 5-[2,2-$Cl_2$-$cC_3H_3$] | $OCH_3$ |
| A-293 | $CH_2$-$cC_3H_5$ | 3-Cl, 5-$OCF_3$ | $OCH_3$ |
| A-294 | $CH_2$-$cC_3H_5$ | 3-Br, 5-$OCF_3$ | $OCH_3$ |
| A-295 | $CH_2$-$cC_3H_5$ | 3-F, 5-$cC_3H_5$ | $OCH_3$ |
| A-296 | $CH_2$-$cC_3H_5$ | 3-Cl, 5-$CH_2CN$ | $OCH_3$ |
| A-297 | $CH_2$-$cC_3H_5$ | 3-Cl, 5-$C(CH_3)_2CN$ | $OCH_3$ |
| A-298 | $CH_2$-$cC_3H_5$ | 3-$CF_3$, 5-$CH_2CN$ | $OCH_3$ |
| A-299 | $CH_2$-$cC_3H_5$ | 3-$CF_3$, 5-$C(CH_3)_2CN$ | $OCH_3$ |
| A-300 | $CH_2$-$cC_3H_5$ | 3-$CF_3$, 5-$SO_2CH_3$ | $OCH_3$ |
| A-301 | $CH_2$-$cC_3H_5$ | 3-$CF_3$, 5-$SO_2CF_3$ | $OCH_3$ |
| A-302 | $CH_2$-$cC_3H_5$ | 3-$CF_3$, 5-$OCF_3$ | $OCH_3$ |
| A-303 | $CH_2$-$cC_3H_5$ | 3-$CF_3$, 5-$cC_3H_5$ | $OCH_3$ |
| A-304 | $CH_2$-$cC_3H_5$ | 3-Cl, 5-[(1-CN)$cC_3H_4$] | $OCH_3$ |
| A-305 | $CH_2$-$cC_3H_5$ | 3-$CF_3$, 5-[(1-CN)$cC_3H_4$] | $OCH_3$ |
| A-306 | $CH_2$-$cC_3H_5$ | 3-$CF_3$, 5-[(2,2-$Cl_2$)-$cC_3H_3$] | $OCH_3$ |
| A-307 | $CH_2$-$cC_3H_5$ | 3-$OCF_3$, 5-$cC_3H_5$ | $OCH_3$ |
| A-308 | $CH_2$-$cC_3H_5$ | 3,5-$SO_2CH_3$ | $OCH_3$ |
| A-309 | $CH_2$-$cC_3H_5$ | 3,5-$SO_2CF_3$ | $OCH_3$ |
| A-310 | $CH_2$-$cC_3H_5$ | 3-Cl, 5-$OC_6H_5$ | $OCH_3$ |
| A-311 | $CH_2$-$cC_3H_5$ | 3-$CF_3$, 5-$OC_6H_5$ | $OCH_3$ |
| A-312 | $CH_2$-$cC_3H_5$ | 3-$CF_3$, 5-[O-(4-Cl—$C_6H_4$)] | $OCH_3$ |
| A-313 | H | 3,5-$F_2$ | $CF_3$ |
| A-314 | H | 3,5-$Cl_2$ | $CF_3$ |
| A-315 | H | 3,5-$Br_2$ | $CF_3$ |
| A-316 | H | 3,5-$I_2$ | $CF_3$ |
| A-317 | H | 3,5-$(CF_3)_2$ | $CF_3$ |
| A-318 | H | 3-Cl, 5-F | $CF_3$ |
| A-319 | H | 3-Cl, 5-Br | $CF_3$ |
| A-320 | H | 3-Cl, 5-I | $CF_3$ |
| A-321 | H | 3-F, 5-CN | $CF_3$ |
| A-322 | H | 3-Cl, 5-CN | $CF_3$ |
| A-323 | H | 3-$CF_3$, 5-CN | $CF_3$ |
| A-324 | H | 3-F, 5-$CF_3$ | $CF_3$ |
| A-325 | H | 3-Cl, 5-$CF_3$ | $CF_3$ |
| A-326 | H | 3-Br, 5-$CF_3$ | $CF_3$ |
| A-327 | H | 3-I, 5-$CF_3$ | $CF_3$ |
| A-328 | H | 3-Cl, 5-$SO_2CH_3$ | $CF_3$ |
| A-329 | H | 3-Cl, 5-$SO_2CF_3$ | $CF_3$ |
| A-330 | H | 3-Cl, 5-$cC_3H_5$ | $CF_3$ |
| A-331 | H | 3-Cl, 5-[2,2-$Cl_2$-$cC_3H_3$] | $CF_3$ |
| A-332 | H | 3-Cl, 5-$OCF_3$ | $CF_3$ |
| A-333 | H | 3-Br, 5-$OCF_3$ | $CF_3$ |
| A-334 | H | 3-F, 5-$cC_3H_5$ | $CF_3$ |
| A-335 | H | 3-Cl, 5-$CH_2CN$ | $CF_3$ |
| A-336 | H | 3-Cl, 5-$C(CH_3)_2CN$ | $CF_3$ |
| A-337 | H | 3-$CF_3$, 5-$CH_2CN$ | $CF_3$ |
| A-338 | H | 3-$CF_3$, 5-$C(CH_3)_2CN$ | $CF_3$ |
| A-339 | H | 3-$CF_3$, 5-$SO_2CH_3$ | $CF_3$ |
| A-340 | H | 3-$CF_3$, 5-$SO_2CF_3$ | $CF_3$ |
| A-341 | H | 3-$CF_3$, 5-$OCF_3$ | $CF_3$ |
| A-342 | H | 3-$CF_3$, 5-$cC_3H_5$ | $CF_3$ |
| A-343 | H | 3-Cl, 5-[(1-CN)$cC_3H_4$] | $CF_3$ |
| A-344 | H | 3-$CF_3$, 5-[(1-CN)$cC_3H_4$] | $CF_3$ |
| A-345 | H | 3-$CF_3$, 5-[(2,2-$Cl_2$)-$cC_3H_3$] | $CF_3$ |
| A-346 | H | 3-$OCF_3$, 5-$cC_3H_5$ | $CF_3$ |
| A-347 | H | 3,5-$SO_2CH_3$ | $CF_3$ |
| A-348 | H | 3,5-$SO_2CF_3$ | $CF_3$ |
| A-349 | H | 3-Cl, 5-$OC_6H_5$ | $CF_3$ |
| A-350 | H | 3-$CF_3$, 5-$OC_6H_5$ | $CF_3$ |
| A-351 | H | 3-$CF_3$, 5-[O-(4-Cl—$C_6H_4$)] | $CF_3$ |
| A-352 | $CH_2$-$cC_3H_5$ | 3,5-$F_2$ | $CF_3$ |
| A-353 | $CH_2$-$cC_3H_5$ | 3,5-$Cl_2$ | $CF_3$ |
| A-354 | $CH_2$-$cC_3H_5$ | 3,5-$Br_2$ | $CF_3$ |
| A-355 | $CH_2$-$cC_3H_5$ | 3,5-$I_2$ | $CF_3$ |
| A-356 | $CH_2$-$cC_3H_5$ | 3,5-$(CF_3)_2$ | $CF_3$ |
| A-357 | $CH_2$-$cC_3H_5$ | 3-Cl, 5-F | $CF_3$ |
| A-358 | $CH_2$-$cC_3H_5$ | 3-Cl, 5-Br | $CF_3$ |
| A-359 | $CH_2$-$cC_3H_5$ | 3-Cl, 5-I | $CF_3$ |
| A-360 | $CH_2$-$cC_3H_5$ | 3-F, 5-CN | $CF_3$ |
| A-361 | $CH_2$-$cC_3H_5$ | 3-Cl, 5-CN | $CF_3$ |
| A-362 | $CH_2$-$cC_3H_5$ | 3-$CF_3$, 5-CN | $CF_3$ |
| A-363 | $CH_2$-$cC_3H_5$ | 3-F, 5-$CF_3$ | $CF_3$ |
| A-364 | $CH_2$-$cC_3H_5$ | 3-Cl, 5-$CF_3$ | $CF_3$ |
| A-365 | $CH_2$-$cC_3H_5$ | 3-Br, 5-$CF_3$ | $CF_3$ |
| A-366 | $CH_2$-$cC_3H_5$ | 3-I, 5-$CF_3$ | $CF_3$ |
| A-367 | $CH_2$-$cC_3H_5$ | 3-Cl, 5-$SO_2CH_3$ | $CF_3$ |

TABLE A-continued

| No. | $R^1$ | $(R^3)_n$ | $R^5$ |
|---|---|---|---|
| A-368 | $CH_2$-$cC_3H_5$ | 3-Cl, 5-$SO_2CF_3$ | $CF_3$ |
| A-369 | $CH_2$-$cC_3H_5$ | 3-Cl, 5-$cC_3H_5$ | $CF_3$ |
| A-370 | $CH_2$-$cC_3H_5$ | 3-Cl, 5-[2,2-$Cl_2$-$cC_3H_3$] | $CF_3$ |
| A-371 | $CH_2$-$cC_3H_5$ | 3-Cl, 5-$OCF_3$ | $CF_3$ |
| A-372 | $CH_2$-$cC_3H_5$ | 3-Br, 5-$OCF_3$ | $CF_3$ |
| A-373 | $CH_2$-$cC_3H_5$ | 3-F, 5-$cC_3H_5$ | $CF_3$ |
| A-374 | $CH_2$-$cC_3H_5$ | 3-Cl, 5-$CH_2CN$ | $CF_3$ |
| A-375 | $CH_2$-$cC_3H_5$ | 3-Cl, 5-$C(CH_3)_2CN$ | $CF_3$ |
| A-376 | $CH_2$-$cC_3H_5$ | 3-$CF_3$, 5-$CH_2CN$ | $CF_3$ |
| A-377 | $CH_2$-$cC_3H_5$ | 3-$CF_3$, 5-$C(CH_3)_2CN$ | $CF_3$ |
| A-378 | $CH_2$-$cC_3H_5$ | 3-$CF_3$, 5-$SO_2CH_3$ | $CF_3$ |
| A-379 | $CH_2$-$cC_3H_5$ | 3-$CF_3$, 5-$SO_2CF_3$ | $CF_3$ |
| A-380 | $CH_2$-$cC_3H_5$ | 3-$CF_3$, 5-$OCF_3$ | $CF_3$ |
| A-381 | $CH_2$-$cC_3H_5$ | 3-$CF_3$, 5-$cC_3H_5$ | $CF_3$ |
| A-382 | $CH_2$-$cC_3H_5$ | 3-Cl, 5-[(1-CN)$cC_3H_4$] | $CF_3$ |
| A-383 | $CH_2$-$cC_3H_5$ | 3-$CF_3$, 5-[(1-CN)$cC_3H_4$] | $CF_3$ |
| A-384 | $CH_2$-$cC_3H_5$ | 3-$CF_3$, 5-[(2,2-$Cl_2$)-$cC_3H_3$] | $CF_3$ |
| A-385 | $CH_2$-$cC_3H_5$ | 3-$OCF_3$, 5-$cC_3H_5$ | $CF_3$ |
| A-386 | $CH_2$-$cC_3H_5$ | 3,5-$SO_2CH_3$ | $CF_3$ |
| A-387 | $CH_2$-$cC_3H_5$ | 3,5-$SO_2CF_3$ | $CF_3$ |
| A-388 | $CH_2$-$cC_3H_5$ | 3-Cl, 5-$OC_6H_5$ | $CF_3$ |
| A-389 | $CH_2$-$cC_3H_5$ | 3-$CF_3$, 5-$OC_6H_5$ | $CF_3$ |
| A-390 | $CH_2$-$cC_3H_5$ | 3-$CF_3$, 5-[O-(4-Cl—$C_6H_4$)] | $CF_3$ |

The term "compound(s) of the invention" refers to compound(s) of formula I, or "compound(s) I", and includes their salts, tautomers, stereoisomers, and N-oxides.

The invention also relates to agrochemical compositions comprising an auxiliary and at least one compound 1.

An agrochemical composition comprises a pesticidally effective amount of a compound 1.

An agrochemical composition comprises a pesticidally effective amount of a compound 1.

The compounds I can be converted into customary types of agro-chemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials e.g. seeds (e.g. GF). These and further compositions types are defined in the "Catalogue of pesticide formulation types and international coding system", Technical Monograph No. 2, 6th Ed. May 2008, CropLife International.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents. Suitable solid carriers or fillers are mineral earths.

Suitable surfactants are surface-active compounds, e.g. anionic, cationic, nonionic, and amphoteric surfactants, block polymers, polyelectrolytes. Such surfactants can be used as emulsifier, dispersant, solubilizer, wetter, penetration enhancer, protective colloid, or adjuvant. Surfactants are listed in McCutcheon's, Vol. 1: Emulsifiers & Detergents, McCutcheon's Directories, Glen Rock, USA, 2008 (International or North American Ed.). Suitable anionic surfactants are alkali, alkaline earth, or ammonium salts of sulfonates, sulfates, phosphates, carboxylates. Suitable nonionic surfactants are alkoxylates, N-substituted fatty acid amides, amine oxides, esters, sugar-based surfactants, polymeric surfactants. Suitable cationic surfactants are quaternary surfactants.

The agrochemical compositions generally comprise between 0.01 and 95%, preferably between 0.1 and 90%, and most preferably between 0.5 and 75%, by weight of active substance.

The active substances are employed in a purity of from 90% to 100%, preferably from 95% to 100%.

Various types of oils, wetters, adjuvants, or fertilizer may be added to the active substances or the compositions comprising them as premix or, if appropriate not until immediately prior to use (tank mix). These agents can be admixed with the compositions according to the invention in a weight ratio of 1:100 to 100:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters of the ready-to-use spray liquor are applied per hectare of agricultural useful area.

The compounds I are suitable for use in protecting crops, plants, plant propagation materials, e.g. seeds, or soil or water, in which the plants are growing, from attack or infestation by animal pests. Therefore, the invention also relates to a plant protection method, which comprises contacting crops, plants, plant propagation materials, e.g. seeds, or soil or water, in which the plants are growing, to be protected from attack or infestation by animal pests, with a pesticidally effective amount of a compound I.

The compounds I are also suitable for use in combating or controlling animal pests. Therefore, the invention also relates to a method of combating or controlling animal pests, which comprises contacting the animal pests, their habitat, breeding ground, or food supply, or the crops, plants, plant propagation materials, e.g. seeds, or soil, or the area, material or environment in which the animal pests are growing or may grow, with a pesticidally effective amount of a compound I.

The compounds I are effective through both contact and ingestion to any and all developmental stages, such as egg, larva, pupa, and adult.

The compounds I can be applied as such or in form of compositions comprising them.

The application can be carried out both before and after the infestation of the crops, plants, plant propagation materials by the pests.

The term "contacting" includes both direct contact (applying the compounds/compositions directly on the animal pest or plant) and indirect contact (applying the compounds/compositions to the locus).

The term "animal pest" includes arthropods, gastropods, and nematodes. Preferred animal pests according to the invention are arthropods, preferably insects and arachnids, in particular insects.

The term "plant" includes cereals, e.g. durum and other wheat, rye, barley, triticale, oats, rice, or maize (fodder maize and sugar maize/sweet and field corn); beet, e.g. sugar beet, or fodder beet; fruits, e.g. pomes, stone fruits, or soft fruits, e.g. apples, pears, plums, peaches, nectarines, almonds, cherries, papayas, strawberries, raspberries, blackberries or gooseberries; leguminous plants, e.g. beans, lentils, peas, alfalfa, or soybeans; oil plants, e.g. rapeseed (oilseed rape), turnip rape, mustard, olives, sunflowers, coconut, cocoa beans, castor oil plants, oil palms, ground nuts, or soybeans; cucurbits, e.g. squashes, pumpkins, cucumber or melons; fiber plants, e.g. cotton, flax, hemp, or jute; citrus fruit, e.g. oranges, lemons, grapefruits or mandarins; vegetables, e.g. eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, e.g. avocados, cinnamon, or camphor; energy and raw material plants, e.g. corn, soybean, rapeseed, sugar cane or oil palm; tobacco; nuts, e.g. walnuts; pistachios; coffee; tea; bananas; vines; hop; sweet leaf (*Stevia*); natural rubber plants or ornamental and forestry plants, shrubs, broad-leaved trees or evergreens, *eucalyptus*; turf; lawn; grass. Preferred plants include potatoes, sugar beets, tobacco, wheat, rye, barley, oats, rice, corn, cotton, soybeans, rapeseed, legumes, sunflowers, coffee, or sugar cane; fruits; vines; ornamentals; or vegetables, e.g. cucumbers, tomatoes, beans or squashes.

The term “seed” embraces seeds and plant propagules including true seeds, seed pieces, suckers, corms, bulbs, fruit, tubers, grains, cuttings, cut shoots, and means preferably true seeds.

“Pesticidally effective amount” means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions e.g. desired pesticidal effect and duration, weather, target species, locus, mode of application.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare.

The compounds I are also suitable for use against non-crop insect pests. For use against said non-crop pests, compounds I can be used as bait composition, gel, general insect spray, aerosol, as ultra-low volume application and bed net (impregnated or surface applied).

The term “non-crop insect pest” refers to pests, which are particularly relevant for non-crop targets, e.g. ants, termites, wasps, flies, ticks, mosquitoes, bed bugs, crickets, or cockroaches, such as: *Aedes aegypti, Musca domestica*, Tribolium spp.; termites such as *Reticulitermes flavipes, Coptotermes formosanus*; roaches such as *Blatella germanica, Periplaneta Americana*; ants such as *Solenopsis invicta, Linepithema humile*, and *Camponotus pennsylvanicus.*

The bait can be a liquid, a solid or a semisolid preparation (e.g. a gel). For use in bait compositions, the typical content of active ingredient is from 0.001 wt % to 15 wt %, desirably from 0.001 wt % to 5 wt % of active compound.

The compounds I and its compositions can be used for protecting wooden materials such as trees, board fences, sleepers, frames, artistic artifacts, etc. and buildings, but also construction materials, furniture, leathers, fibers, vinyl articles, electric wires and cables etc. from ants, termites and/or wood or textile destroying beetles, and for controlling ants and termites from doing harm to crops or human beings (e.g. when the pests invade into houses and public facilities or nest in yards, orchards or parks).

Customary application rates in the protection of materials are, e.g., from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 wt %, preferably from 0.1 to 45 wt %, and more preferably from 1 to 25 wt % of at least one repellent and/or insecticide.

The compounds of the invention are especially suitable for efficiently combating animal pests e.g. arthropods, and nematodes including:

- insects from the sub-order of Auchenorrhyncha, e.g. Amrasca biguttula, *Empoasca* spp., *Nephotettix virescens, Sogatella furcifera, Mahanarva* spp., *Laodelphax striatellus, Nilaparvata lugens, Diaphorina citri;*
- Lepidoptera, e.g. *Helicoverpa* spp., *Heliothis virescens, Lobesia botrana, Ostrinia nubilalis, Plu-tella xylostella, Pseudoplusia includens, Scirpophaga incertulas, Spodoptera* spp., *Trichoplusia ni, Tuta absoluta, Cnaphalocrocis medialis, Cydia pomonella, Chilo suppressalis, Anticarsia gemmatalis, Agrotis ipsilon, Chrysodeixis includens;*
- True bugs, e.g. *Lygus* spp., Stink bugs such as *Euschistus* spp., *Halyomorpha halys, Nezara viridula, Piezodorus guildinii, Dichelops furcatus;*
- *Thrips*, e.g. *Frankliniella* spp., *Thrips* spp., *Dichromothrips corbettii;*
- Aphids, e.g. *Acyrthosiphon pisum, Aphis* spp., *Myzus persicae, Rhopalosiphum* spp., *Schizaphis graminum, Megoura viciae;*
- Whiteflies, e.g. *Trialeurodes vaporariorum, Bemisia* spp.;
- Coleoptera, e.g. *Phyllotreta* spp., Melanotus spp., *Meligethes aeneus, Leptinotarsa decimlineata, Ceutorhynchus* spp., *Diabrotica* spp., *Anthonomus grandis, Atomarialinearia, Agriotes* spp., *Epilachna* spp.;
- Flies, e.g. *Delia* spp., *Ceratitis* capitate, Bactrocera spp., *Liriomyza* spp.;
- Mosquitoes (Diptera), e.g. *Aedes aegypti, A. albopictus, A. vexans, Anastrepha ludens, Anopheles maculipennis, A. crucians, A. albimanus, A. gambiae, A. freeborni, A. leucosphyrus, A. minimus, A. quadrimaculatus;*
- *Coccoidea*, e.g. *Aonidiella aurantia, Ferrisia virgate;*
- Anthropods of class Arachnida (Mites), e.g. *Penthaleus major, Tetranychus* spp.;
- Nematodes, e.g. *Heterodera glycines, Meloidogyne* sp., *Pratylenchus* spp., *Caenorhabditis elegans.*

The compounds I are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound I.

The invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound I.

The compounds of the invention are further suitable for use in combating or controlling parasites in and on animals. Furthermore, the invention relates to a method of combating or controlling parasites in and on animals, which comprises contacting the parasites with a parasitically effective amount of a compound I.

The invention also relates to the non-therapeutic use of compounds I for controlling or combating parasites. Moreover, the invention relates to a non-therapeutic method of combating or controlling parasites, which comprises applying to a locus a parasiticidally effective amount of a compound I.

The compounds I can be effective through both contact (via soil, glass, wall, bed net, carpet, blankets, or animal parts) and ingestion (e.g. baits). Furthermore, the compounds I can be applied to any and all developmental stages.

The compounds I can be applied as such or in form of compositions comprising them.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include lice, biting lice, ticks, nasal bots, keds, biting flies, muscoid flies, flies, myiasitic fly larvae, chiggers, gnats, mosquitoes and fleas.

The compounds of the invention are especially useful for combating the following parasites: *Cimex lectularius, Rhipicephalus sanguineus*, and *Ctenocephalides felis.*

As used herein, the term "animal" includes warm-blooded animals (including humans) and fish.

Preferred are mammals, such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Particularly preferred are domestic animals, such as dogs or cats.

The compounds I may be applied in total amounts of 0.5 mg/kg to 100 mg/kg per day, preferably 1 mg/kg to 50 mg/kg per day.

For oral administration to warm-blooded animals, the compounds I may be formulated as animal feeds, animal feed premixes, animal feed concentrates, pills, solutions, pastes, suspensions, drenches, gels, tablets, boluses and capsules. For oral administration, the dosage form chosen should provide the animal with 0.01 mg/kg to 100 mg/kg of animal body weight per day of the compounds I, preferably with 0.5 mg/kg to 100 mg/kg of animal body weight per day.

Alternatively, the compounds I may be administered to animals parenterally, e.g., by intraruminal, intramuscular, intravenous or subcutaneous injection. The compounds I may be dispersed or dissolved in a physiologically acceptable carrier for subcutaneous injection. Alternatively, the compounds I may be formulated into an implant for subcutaneous administration. In addition, the compounds I may be transdermally administered to animals. For parenteral administration, the dosage form chosen should provide the animal with 0.01 mg/kg to 100 mg/kg of animal body weight per day of the compounds I.

The compounds I may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds I. In addition, the compounds I may be formulated as ear tags for animals, particularly quadrupeds e.g. cattle and sheep.

Oral solutions are administered directly.

Solutions for use on the skin are trickled on, spread on, rubbed in, sprinkled on or sprayed on.

Gels are applied to or spread on the skin or introduced into body cavities.

Pour-on formulations are poured or sprayed onto limited areas of the skin, the active compound penetrating the skin and acting systemically. Pour-on formulations are prepared by dissolving, suspending, or emulsifying the active compound in suitable skin-compatible solvents or solvent mixtures.

Emulsions can be administered orally, dermally or as injections.

Suspensions can be administered orally or topically/dermally.

Semi-solid preparations can be administered orally or topically/dermally.

For the production of solid preparations, the active compound is mixed with suitable excipients, if appropriate with addition of auxiliaries, and brought into the desired form.

The compositions which can be used in the invention can comprise generally from about 0.001 to 95% of the compound I.

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40% by weight.

Preparations which are diluted before use contain the compounds acting against ectoparasites in concentrations of 0.5 to 90% by weight, preferably of 1 to 50% by weight.

Furthermore, the preparations comprise the compounds of formula I against endoparasites in concentrations of 10 ppm to 2% by weight, preferably of 0.05 to 0.9% by weight, very particularly preferably of 0.005 to 0.25% by weight.

Solid formulations which release compounds of the invention may be applied in total amounts of 10 mg/kg to 300 mg/kg, preferably 20 mg/kg to 200 mg/kg, most preferably 25 mg/kg to 160 mg/kg body weight of the treated animal in the course of three weeks.

A. PREPARATION EXAMPLES

The compounds were characterized by melting point determination, by NMR spectroscopy or by the mass-to-charge ratio ([m/z]) and retention time (RT; [min.]), as determined by mass spectrometry (MS) coupled with HPLC analysis (HPLC-MS=high performance liquid chromatography-coupled mass spectrometry) or LC analysis (LC-MS=liquid chromatography-coupled mass spectrometry).

Method A: HPLC: Shimadzu Nexera UHPLC+Shimadzu LCMS-2020, ESI; Column: Phenomenex Kinetex 1.7 μm XB—C18 100A, 2.1×50 mm; Mobile phase: A: water+0.1% TFA; B: ACN; Temperature: 60° C.; Gradient: 5% B to 100% B in 1.5 min; 100% B 0.25 min; Flow: 0.8 mL/min to 1.0 mL/min in 1.51 min; MS: ESI positive; Mass range (m/z): 100-700.

Method B: LC: Shimadzu LC-30AD, ESI; Column: Kinetex EVO C18.5 μm 2.1×30 mm; Mobile phase: A: water+0.04% TFA; B: ACN+0.02% TFA; Temperature: 40° C.; Gradient: 5% B to 100% B in 2.5 min; 100% B to 5% B in 0.02 min; 5% B for 0.5 min; Flow: 0.8 mL/min; MS: ESI positive; Mass range: 100-2000.

Method C: HPLC/MS: Agilent 1200 HPLC MSD:1956A single quadrupole MSD, ES-API; Column: Luna C18 2.0×50 mm 5 μm; Mobile phase: A: 0.04% TFA in water; B: 0.02% TFA in ACN; Temperature: 40° C.; Gradient: 5% B for 0.4 min; 5% B to 95% B in 2.6 min; 95% B for 1 min; 95% B to 5% B in 0.01 min; 5% B for 0.5 min; Flow: 1.0 mL/min; MS: ES-API positive; Mass range: 50-1500.

Method D: HPLC/MS: Agilent 1200 HPLC MSD:6120 single quadrupole MSD; Column: XBridge C18 2.1×50 mm 5 μm; Mobile phase: A: 10 nM NH4HCO3 in water; B: ACN; Temperature: 40° C.; Gradient: 5% B to 95% B in 3.4 min; 95% B for 0.45 min; 95% B to 5% B in 0.01 min; 5% B for 0.64 min; Flow: 0.8 mL/min; MS: ES-API positive; Mass range: 50-2000.

Example 1: Preparation of 3-bromo-N-[1-[3-(4-methyl-5-oxo-1,2,4-triazol-1-yl)pyrazin-2-yl]ethyl]-5-(trifluoromethyl)benzamide (1-1)

Step 1: Preparation of 2-[(3-chloropyrazin-2-yl)hydrazono]acetic acid

To a solution of (3-chloropyrazin-2-yl)hydrazine (5 g, 0.0346 mol) in aq. HCl (6N, 10 mL) was added glyoxylic acid (3.18 g, 0.0346 mol) at 20° C. The mixture was stirred at 80° C. for 12 h, during which time a yellow precipitate was formed. Completion was determined by LCMS. The mixture was filtered and the filter cake was dried to furnish 2-[(3-chloropyrazin-2-yl)hydrazono]acetic acid (6.2 g, 89% yield) as a yellow solid.

$^1$H-NMR (400 MHz, DMSO-$d_6$) δ=8.02 (s, 1H), 8.22 (d, J=2.5 Hz, 1H), 8.51 (d, J=2.5 Hz, 1H), 11.35-11.83 (m, 1H).

Step 2: Preparation of 2-(3-chloropyrazin-2-yl)-4H-1,2,4-triazol-3-one

To a suspension of 2-[(3-chloropyrazin-2-yl)hydrazono]acetic acid (3 g, 0.0149 mol) in THE (50 mL) were added trimethylsilyl azide (2.24 g, 0.0194 mol), propanephosphonic acid anhydride (T3P, 6.19 g, 0.0194 mol), and diisopropylethylamine (5.79 g, 0.0449 mol) at 20° C. The mixture was stirred at 80° C. for 12 h, at which time completion was determined by LCMS. The volatiles were removed under reduced pressure and the residue was purified by preparative HPLC ($NH_4HCO_3$) to deliver 2-(3-chloropyrazin-2-yl)-4H-1,2,4-triazol-3-one (740 mg, 25% yield) as a yellow solid.

$^1$H-NMR (400 MHz, $CDCl_3$) δ=7.72 (s, 1H), 8.52 (d, J=2.3 Hz, 1H), 8.55-8.59 (m, 1H).

Step 3: Preparation of 2-(3-chloropyrazin-2-yl)-4-methyl-1,2,4-triazol-3-one

To a solution of 2-(3-chloropyrazin-2-yl)-4H-1,2,4-triazol-3-one (1.3 g, 0.0067 mol) in acetonitrile (100 mL) were added $CH_3I$ (1.87 g, 0.0132 mol) and $K_2CO_3$ (1.7 g, 0.0132 mol) at 20° C. The mixture was stirred at 25° C. for 48 h, at which time completion was determined by TLC (EtOAc). The reaction mixture was quenched with $H_2O$ (100 mL) and extracted with EtOAc (3×30 mL). The combined organic layers were washed with brine (20 mL), dried over $Na_2SO_4$, and concentrated. The residue was purified by chromatographic column on silica gel (eluent PE:EtOAc=100:0 to 10:90) to furnish 2-(3-chloropyrazin-2-yl)-4-methyl-1,2,4-triazol-3-one (0.47 g, 34% yield) as a yellow solid.

$^1$H-NMR (400 MHz, $CDCl_3$) δ=3.41 (s, 3H), 7.65 (s, 1H), 8.48 (d, J=2.4 Hz, 1H), 8.53 (d, J=2.4 Hz, 1H).

Step 4: Preparation of 2-[3-(1-ethoxyvinyl)pyrazin-2-yl]-4-methyl-1,2,4-triazol-3-one To a mixture of 2-(3-chloropyrazin-2-yl)-4-methyl-1,2,4-triazol-3-one (0.47 g, 0.00222 mol) in toluene (50 mL) were added tributyl(1-ethoxyvinyl)stannane (0.802 g, 0.00222 mol) and $Pd(PPh_3)_2Cl_2$ (156 mg) at 25° C. The mixture was stirred for 12 h at 100° C., at which time completion was determined by LCMS. After cooling the reaction mixture to 25° C., aq. sat. KF (30 mL) was added and stirred for 30 min. The mixture was filtered through a celite pad, and the filtrate was extracted with EtOAc (3×30 mL). The combined organic layers were washed with brine (10 mL), dried over $Na_2SO_4$, and concentrated. The residue was purified by chromatographic column on silica gel (PE:EtOAc=100:0 to 5:95) to deliver 2-[3-(1-ethoxyvinyl)pyrazin-2-yl]-4-methyl-1,2,4-triazol-3-one (0.25 g, 46% yield) as an yellow oil, which was employed in the next step without further purification.

Step 5: Preparation of 2-(3-acetylpyrazin-2-yl)-4-methyl-1,2,4-triazol-3-one

To a solution of 2-[3-(1-ethoxyvinyl)pyrazin-2-yl]-4-methyl-1,2,4-triazol-3-one (0.25 g, 0.001 mol) in THF (3 mL) was added aq. HCl (2M, 3 mL) dropwise at 25° C. The resulting mixture was stirred for 16 h at 25° C., at which time completion was determined by LCMS. The reaction mixture was diluted with $H_2O$ (50 mL) and extracted with EtOAc (3×20 mL). The combined organic layers were washed with brine (40 mL), dried over $Na_2SO_4$, and concentrated to furnish 2-(3-acetylpyrazin-2-yl)-4-methyl-1,2,4-triazol-3-one (0.18 g, crude) as a yellow oil.

$^1$H-NMR (400 MHz, $CDC_3$) δ=2.79 (s, 3H), 3.36 (s, 3H), 7.66 (s, 1H), 8.57 (d, J=2.4 Hz, 1H), 8.66 (d, J=2.4 Hz, 1H).

Step 6: Preparation of 2-[3-(1-aminoethyl)pyrazin-2-yl]-4-methyl-1,2,4-triazol-3-one To a solution of 2-(3-acetylpyrazin-2-yl)-4-methyl-1,2,4-triazol-3-one (0.15 g, 0.684 mmol) in MeOH (5 mL) were added $NH_4OAc$ (0.527 g, 0.6.84 mmol), $NaBH_3CN$ (86 mg, 0.136 mmol), and $NH_3$ (7N in MeOH, 2 mL) at 20° C. The resulting mixture was stirred for 16 h at 20° C., at which time completion was determined by TLC (DCM:MeOH=10:1). The volatiles were removed under reduced pressure and $H_2O$ (50 mL) was added. The pH of the resulting solution was adjusted to 10 by addition of aq. NaOH, and the mixture was extracted with DCM/iPrOH (3/1, 3×20 mL). The combined organic layers were dried over $Na_2SO_4$ and concentrated to deliver 2-[3-(1-aminoethyl)pyrazin-2-yl]-4-methyl-1,2,4-triazol-3-one (50 mg, crude) as a yellow oil, which was employed in the next step without further purification.

Step 7: Preparation of 3-bromo-N-[1-[3-(4-methyl-5-oxo-1,2,4-triazol-1-yl)pyrazin-2-yl]ethyl]-5-(trifluoromethyl)benzamide (1-1)

To a solution of 3-bromo-5-(trifluoromethyl)benzoic acid (0.489 g, 0.00182 mol) in acetonitrile (10 mL) were added N'-tetramethylformamidinium hexafluorophosphate (0.765 g, 0.00273 mol), N-methylimidazole (0.448 g, 0.0055 mol), and 2-[3-(1-aminoethyl)pyrazin-2-yl]-4-methyl-1,2,4-triazol-3-one (0.4 g, 0.00182 mol) at 20° C. The mixture was stirred at 20° C. for 0.5 h, at which time completion was determined by LCMS. The reaction mixture was quenched with $H_2O$ (10 mL) and extracted with EtOAc (3×30 mL).

The combined organic layers were washed with brine (10 mL), dried over $Na_2SO_4$, and concentrated. The residue was purified by preparative HPLC ($NH_4HCO_3$) to deliver 3-bromo-N-[1-[3-(4-methyl-5-oxo-1,2,4-triazol-1-yl) pyrazin-2-yl]ethyl]-5-(trifluoromethyl)benzamide (1-1, 0.2 g, 23% yield) as a pink solid.

$^1$H-NMR (400 MHz, $CDCl_3$) δ=1.62 (d, J=6.6 Hz, 3H), 3.44 (s, 3H), 5.65-5.80 (m, 1H), 7.40 (br d, J=7.4 Hz, 1H), 7.67 (s, 1H), 7.89 (s, 1H), 7.98 (s, 1H), 8.11 (s, 1H), 8.59 (d, J=2.0 Hz, 1H), 8.67 (d, J=2.0 Hz, 1H).

LCMS: calculated mass: 471; observed mass: 471.473.

Example 2: Preparation of 3-bromo-N-[1-[3-[5-oxo-4-(2,2,2-trifluoroethyl)-1,2,4-triazol-1-yl]pyrazin-2-yl]ethyl]-5-(trifluoromethyl)benzamide (1-2)

Step 1: Preparation of 2-(3-chloropyrazin-2-yl)-4-(2,2,2-trifluoroethyl)-1,2,4-triazol-3-one To a solution of 2-(3-chloropyrazin-2-yl)-4H-1,2,4-triazol-3-one (1.2 g, 0.0061 mol) in acetonitrile (100 mL) were added 2,2,2-trifluoroethyl trifluoromethanesulfonate (1.4 g, 0.0061 mol) and $K_2CO_3$ (1.57 g, 0.0122 mol) at 20° C. The resulting mixture was stirred at 25° C. for 12 h, at which time the product was the major component of the mixture, as determined by LCMS. The reaction mixture was quenched with $H_2O$ (50 mL) and extracted with EtOAc (3×20 mL). The combined organic layers were washed with brine (40 mL), dried over $Na_2SO_4$, and concentrated. The residue was purified by chromatographic column on silica gel (PE:EtOAc=100:0 to 35:75) to furnish 2-(3-chloropyrazin-2-yl)-4-(2,2,2-trifluoroethyl)-1,2,4-triazol-3-one (1.2 g, 71% yield) as a white solid.

$^1$H-NMR (400 MHz, $CDC_3$) δ=4.37 (q, J=8.5 Hz, 2H), 7.78 (s, 1H), 8.52 (d, J=2.4 Hz, 1H), 8.56 (d, J=2.4 Hz, 1H).

Step 2: Preparation of 2-[3-(1-ethoxyvinyl)pyrazin-2-yl]-4-(2,2,2-trifluoroethyl)-1,2,4-triazol-3-one To a solution of 2-(3-chloropyrazin-2-yl)-4-(2,2,2-trifluoroethyl)-1,2,4-triazol-3-one (0.2 g, 0.715 mmol) in toluene (10 mL) were added tributyl(1-ethoxyvinyl)stannane (0.258 g, 0.715 mmol) and $Pd(PPh_3)_2Cl_2$ (50 mg) at 25° C. The resulting mixture was stirred for at 100° C. for 12 h, at which time completion was determined by LCMS, then cooled to 25° C. The mixture was diluted with aq. sat. KF (20 mL), stirred for 30 min, and filtered through a celite pad. The filtrate was extracted with EtOAc (3×30 mL) and the combined organic layers were washed with brine (10 mL), dried over $Na_2SO_4$, and concentrated. The residue was purified by chromatographic column on silica gel (PE:EtOAc=100:0 to 65:35) to deliver 2-[3-(1-ethoxyvinyl)pyrazin-2-yl]-4-(2,2,2-trifluoroethyl)-1,2,4-triazol-3-one (0.1 g, 44% yield) as a yellow oil, which was employed in the next step without further purification.

Step 3: Preparation of 2-(3-acetylpyrazin-2-yl)-4-(2,2,2-trifluoroethyl)-1,2,4-triazol-3-one To a solution of 2-[3-(1-ethoxyvinyl)pyrazin-2-yl]-4-(2,2,2-trifluoroethyl)-1,2,4-triazol-3-one (0.1 g, 0.317 mmol) in THF (3 mL) was added aq. HCl (2M, 3 mL) dropwise at 0° C. The resulting mixture was stirred for 16 h at 25° C., at which time completion was determined by LCMS. The reaction mixture was quenched with $H_2O$ (5 mL) and extracted with EtOAc (3×20 mL). The combined organic layers were washed with brine (4 mL), dried over $Na_2SO_4$, and concentrated. The residue was purified by preparative TLC (EtOAc) to furnish 2-(3-acetylpyrazin-2-yl)-4-(2,2,2-trifluoroethyl)-1,2,4-triazol-3-one (50 mg, 50% yield) as a yellow solid.

$^1$H-NMR (400 MHz, $CDC_3$) δ=2.78 (s, 3H), 4.31 (q, J=8.5 Hz, 2H), 7.78 (s, 1H), 8.63 (d, J=2.4 Hz, 1H), 8.69 (d, J=2.4 Hz, 1H).

Step 4: Preparation of 2-[3-(1-aminoethyl)pyrazin-2-yl]-4-(2,2,2-trifluoroethyl)-1,2,4-triazol-3-one To a solution of 2-(3-acetylpyrazin-2-yl)-4-(2,2,2-trifluoroethyl)-1,2,4-triazol-3-one (0.4 g, 1.39 mmol) in MeOH (50 mL) were added $NH_4OAc$ (1.07 g, 13.9 mmol), $NaBH_3CN$ (175 mg, 2.79 mmol) and $NH_3$ (7N in MeOH, 2 mL) at 20° C., and the resulting mixture was stirred at 40° C. for 16 h, at which time completion was determined by TLC (DCM:MeOH=10:1)(aq. $NH_3$). The volatiles were removed under reduced pressure and the residue was taken in $H_2O$ (5 mL). The pH was adjusted to 10 by addition of aq. NaOH, and the resulting solution was extracted with DCM/iPrOH (3/1, 3×20 mL). The combined organic layers were dried over $Na_2SO_4$ and concentrated to deliver 2-[3-(1-aminoethyl)pyrazin-2-yl]-4-(2,2,2-trifluoroethyl)-1,2,4-triazol-3-one (50 mg, crude) as a yellow oil, which was employed in the next step without further purification.

Step 5: Preparation of 3-bromo-N-[1-[3-[5-oxo-4-(2,2,2-trifluoroethyl)-1,2,4-triazol-1-yl]pyrazin-2-yl]ethyl]-5-(trifluoromethyl)benzamide (1-2)

To a solution of 3-bromo-5-(trifluoromethyl)benzoic acid (0.448 g, 0.00156 mol) in acetonitrile (10 mL) were added N'-tetramethylformamidinium hexafluorophosphate (0.438 g, 0.00156 mol), N-methylimidazole (0.256 g, 0.0031 mol) and 2-[3-(1-aminoethyl)pyrazin-2-yl]-4-(2,2,2-trifluoroethyl)-1,2,4-triazol-3-one (0.3 g, 0.00104 mol) at 20° C., and the resulting mixture was stirred for 0.5 h at which time completion was determined by LCMS. The reaction mixture was quenched with $H_2O$ (10 mL) and extracted with EtOAc (3×30 mL). The combined organic layers were washed with brine (10 mL), dried over $Na_2SO_4$, and concentrated. The residue was purified by preparative HPLC ($NH_4HCO_3$) to deliver 3-bromo-N-[1-[3-[5-oxo-4-(2,2,2-trifluoroethyl)-1,2,4-triazol-1-yl]pyrazin-2-yl]ethyl]-5-(trifluoromethyl)benzamide (1-2, 0.2 g, 36% yield) as a pink solid.

$^1$H-NMR (400 MHz, $CDCl_3$) δ=1.63 (d, J=6.6 Hz, 3H), 4.31-4.48 (m, 2H), 5.70 (dq, J=6.6 Hz, J=7.6 Hz, 1H), 7.32 (br d, J=7.6 Hz, 1H), 7.81 (s, 1H), 7.90 (s, 1H), 7.97 (s, 1H), 8.10 (s, 1H), 8.61 (d, J=2.4 Hz, 1H), 8.70 (d, J=2.4 Hz, 1H).

LCMS: calculated mass: 539; observed mass: 539.541.

Example 3: Preparation of 3-bromo-N-[1-[3-[4-[(4-methoxyphenyl)methyl]-5-oxo-1,2,4-triazol-1-yl] pyrazin-2-yl]ethyl]-5-methylsulfonyl-benzamide (1-3)

Step 1: Preparation of 2-(3-acetylpyrazin-2-yl)-4-[(4-methoxyphenyl)methyl]-1,2,4-triazol-3-one To a solution of 1-(3-chloropyrazin-2-yl)ethanone (4.56 g, 29.2 mmol) in DMF (100 mL) were added 4-[(4-methoxyphenyl)methyl]-1H-1,2,4-triazol-5-one (9 g, 43.9 mmol) and $K_2CO_3$ (6 g, 43.9 mmol) at 20° C. and the resulting mixture was stirred at 80° C. for 12 h, at which time completion was determined by TLC (PE:EtOAc=3:1). The reaction mixture was poured into $H_2O$ (50 mL) and extracted with EtOAc (200 mL×3). The combined organic layers were washed with brine (50 mL×2), dried over $Na_2SO_4$, filtered, concentrated and purified by silicagel column (EtOAc in PE=0% to 100%) to deliver 2-(3-acetylpyrazin-2-yl)-4-[(4-methoxyphenyl)methyl]-1,2,4-triazol-3-one (5 g, 53% yield) as a yellow solid.

$^1$H-NMR (400 MHz, $CDCl_3$): δ=8.65 (d, J=2.38 Hz, 1H), 8.57 (d, J=2.38 Hz, 1H), 7.52 (s, 1H), 7.25 (s, 2H), 6.90-6.94 (m, 2H), 4.77 (s, 2H), 3.82 (s, 3H), 2.81 (s, 3H).

Step 2: Preparation of 2-[3-(1-aminoethyl)pyrazin-2-yl]-4-[(4-methoxyphenyl)methyl]-1,2,4-triazol-3-one To a solution of 2-(3-acetylpyrazin-2-yl)-4-[(4-methoxyphenyl)methyl]-1,2,4-triazol-3-one (5 g, 15.38 mmol) in MeOH (250 mL) were added $NH_4OAc$ (11.85 g, 153.8 mmol), $NH_3$/MeOH (7N, 150 mL) at 25° C. and the resulting mixture was stirred for 1 h. Subsequently, $NaBH_3CN$ (2.9 g, 46.15 mmol) was added portionwise at 0° C. and the mixture was stirred at 50° C. for 12 h, at which time completion was determined by LCMS. The reaction mixture was quenched with $H_2O$ (10 mL), concentrated and extracted with EtOAc (50 mL×3), the organic layer was dried over $Na_2SO_4$ and concentrated to deliver 2-[3-(1-aminoethyl)pyrazin-2-yl]-4-[(4-methoxyphenyl)methyl]-1,2,4-triazol-3-one (5 g) as brown oil. The crude product was employed in the next step without further purification.

$^1$H-NMR (400 MHz, DMSO-$d_6$) δ=8.72-8.82 (m, 1H), 8.55 (d, J=1.50 Hz, 1H), 8.31-8.39 (m, 1H), 7.32 (d, J=8.50 Hz, 2H), 6.96 (br d, J=8.13 Hz, 2H), 4.82 (s, 2H), 4.04 (q, J=6.17 Hz, 1H), 3.75 (s, 3H), 1.20-1.36 (m, 3H).

Step 3: Preparation of 3-bromo-N-[1-[3-[4-[(4-methoxyphenyl)methyl]-5-oxo-1,2,4-triazol-1-yl]pyrazin-2-yl]ethyl]-5-methylsulfonyl-benzamide To a solution of 3-bromo-5-methylsulfonyl-benzoic acid (1.14 g, 4.1 mmol) in DMF (40 mL) were added 2-[3-(1-aminoethyl)pyrazin-2-yl]-4-[(4-methoxyphenyl)methyl]-1,2,4-triazol-3-one (2 g, 6.14 mmol), HATU (2.32 g, 6.14 mmol), and triethylamine (1.03 g, 10.24 mmol) at 20° C. The mixture was stirred for 12 h, at which time completion was determined by TLC (PE:EtOAc=1:1). The mixture was poured into $H_2O$ (100 mL), extracted with EtOAc (50 mL×3), washed with brine (50 mL), dried over $Na_2SO_4$, filtered, and concentrated. The residue was purified by column chromatography (EtOAc in PE=0%-100%) and subsequently triturated with MTBE (10 mL) to furnish 3-bromo-N-[1-[3-[4-[(4-methoxyphenyl)methyl]-5-oxo-1,2,4-triazol-1-yl]pyrazin-2-yl]ethyl]-5-methylsulfonyl-benzamide (1-3, 200 mg, 17% yield) as light pink solid.

$^1$H-NMR (400 MHz, $CDCl_3$) δ=8.52-8.77 (m, 2H), 8.24 (d, J=1.63 Hz, 2H), 8.18-8.22 (m, 1H), 7.51-7.57 (m, 1H), 7.48 (br d, J=7.75 Hz, 1H), 7.30-7.36 (m, 2H), 6.91-6.98 (m, 2H), 5.76 (dq, J=6.94 Hz, 1H), 4.85 (s, 2H), 3.84 (s, 3H), 3.10 (s, 3H), 1.61 (d, J=6.63 Hz, 3H).

Example 4: Preparation of 3-bromo-N-[1-[3-[4-(cyclopropylmethyl)-5-oxo-1,2,4-triazol-1-yl]pyrazin-2-yl]ethyl]-5-methylsulfonyl-benzamide (1-5)

Step 1: Preparation of 3-bromo-5-methylsulfonyl-N-[1-[3-(5-oxo-4H-1,2,4-triazol-1-yl)pyrazin-2-yl]ethyl]benzamide (INT)

To a solution of 3-bromo-N-[1-[3-[4-[(4-methoxyphenyl)methyl]-5-oxo-1,2,4-triazol-1-yl]pyrazin-2-yl]ethyl]-5-methylsulfonyl-benzamide (1-3, 900 mg, 2.70 mmol) in MeCN/$H_2O$ (1:1 v/v, 9 mL) was added ceric ammonium nitrate (3.36 g, 6.14 mmol). The reaction mixture was stirred at 50° C. for 16 h, at which time completion was determined by TLC (EtOAc). The mixture was poured into $H_2O$ (20 mL) and extracted with EtOAc (20 mL×3). The combined organic layers were washed with brine (20 mL), dried over $Na_2SO_4$, filtered, and concentrated. The residue was purified by trituration with MTBE (10 mL) followed by preparative HPLC (neutral, $CH_3CN/H_2O$) to deliver 3-bromo-5-methylsulfonyl-N-[1-[3-(5-oxo-4H-1,2,4-triazol-1-yl)pyrazin-2-yl]ethyl]benzamide (INT, 150 mg, 20% yield) as a yellow solid.

$^1$H-NMR (400 MHz, DMSO-dc): 6=11.91 (br d, J=2.50 Hz, 1H), 9.21 (d, J=7.50 Hz, 1H), 8.77 (d, J=2.38 Hz, 1H), 8.62 (d, J=2.38 Hz, 1H), 8.28-8.36 (m, 2H), 8.18-8.25 (m, 1H), 8.11 (s, 1H), 5.48 (dq, J=6.88, 7.50 Hz, 1H), 3.31 (br s, 3H), 1.56 (d, J=6.88 Hz, 3H).

LCMS: Method B, RT=1.14 min; m/z $[M+H]^+$ calc. 467.0, found 467.0/469.0 (Br isotopes).

Step 2: Preparation of 3-bromo-N-[1-[3-[4-(cyclopropylmethyl)-5-oxo-1,2,4-triazol-1-yl]pyrazin-2-yl]ethyl]-5-methylsulfonyl-benzamide (1-5)

To a solution of 3-bromo-5-methylsulfonyl-N-[1-[3-(5-oxo-4H-1,2,4-triazol-1-yl)pyrazin-2-yl]ethyl]benzamide (INT, 230 mg, 0.494 mmol) in DMF (8 mL) were added $Cs_2CO_3$ (482 mg, 1.48 mmol) and bromomethylcyclopropane (100 mg, 0.74 mmol) at 15° C. The resulting mixture was stirred at 50° C. for 16 h, at which time completion was determined by LCMS. The mixture was poured into $H_2O$ (15 mL) and extracted with EtOAc (50 mL×3). The organic layers were washed with brine (15 mL×3), dried over $Na_2SO_4$, filtered and concentrated. The residue was purified by preparative HPLC (TFA, MeCN/$H_2O$) to deliver 3-bromo-N-[1-[3-[4-(cyclopropylmethyl)-5-oxo-1,2,4-triazol-1-yl]pyrazin-2-yl]ethyl]-5-methylsulfonyl-benzamide (1-5, 150 mg, 58% yield) as a white solid.

$^1$H-NMR (400 MHz, $CDCl_3$) δ=8.66 (d, J=2.38 Hz, 1H), 8.60 (d, J=2.38 Hz, 1H), 8.25 (d, J=1.76 Hz, 2H), 8.20-8.22 (m, 1H), 7.84 (s, 1H), 7.49-7.54 (m, 1H), 5.72-5.80 (m, 1H), 3.62 (d, J=7.28 Hz, 2H), 3.11 (s, 3H), 1.62 (d, J=6.78 Hz, 3H), 1.22-1.27 (m, 1H), 0.71-0.77 (m, 2H), 0.43-0.48 (m, 2H).

Example 5: Preparation of 3-bromo-N-methyl-N-[1-[3-(4-methyl-5-oxo-1,2,4-triazol-1-yl)pyrazin-2-yl]ethyl]-5-methylsulfonyl-benzamide (1-8)

To a solution of 3-bromo-5-methylsulfonyl-N-[1-[3-(5-oxo-4H-1,2,4-triazol-1-yl)pyrazin-2-yl]ethyl]benzamide (INT, 220 mg, 0.471 mmol) in DMF (10 mL) was added NaH (28 mg, 1.177 mmol) at 0° C. The mixture was stirred at 0° C. for 30 min. $CH_3I$ (201 mg, 1.413 mmol) was added. The mixture was stirred at 15° C. for 6 h, at which time completion was determined by LCMS. The reaction mixture was poured into $H_2O$ (30 mL) and extracted with EtOAc (20 mL×3). The organic layers were washed with brine (20 mL×3), dried over $Na_2SO_4$, filtered and concentrated. The residue was purified by preparative HPLC (TFA, MeCN/$H_2O$) to furnish 3-bromo-N-methyl-N-[1-[3-(4-methyl-5-oxo-1,2,4-triazol-1-yl)pyrazin-2-yl]ethyl]-5-methylsulfonylbenzamide (1-8, 78 mg, 33% yield) as a yellow syrup.

$^1$H-NMR (400 MHz, DMSO-$d_6$) δ=8.87 (d, J=2.26 Hz, 1H), 8.74 (d, J=2.26 Hz, 1H), 8.23 (s, 1H), 8.15 (s, 1H), 7.87 (s, 1H), 7.85 (s, 1H), 6.09 (q, J=6.57 Hz, 1H), 3.32 (s, 3H), 3.23 (s, 3H), 2.51-2.52 (m, 3H), 1.58 (d, J=6.78 Hz, 3H).

With appropriate modification of the starting materials, the procedures given in the synthesis descriptions were used to obtain further compounds 1. The compounds obtained in this manner are listed in the table that follows, together with physical data.

TABLE I

Compounds of formula I with $R^2 = CH_3$

I

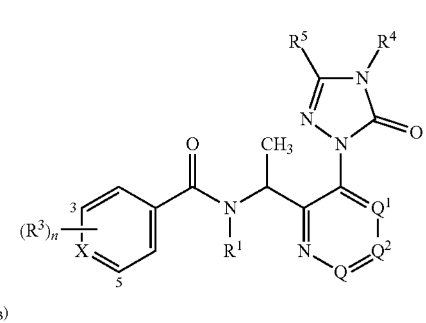

($R^2 = CH_3$)

| No. | $R^1$ | X | $(R^3)_n$ | $R^4$ | $R^5$ | $Q^1$ | $Q^2$ | Q | phys. data Method | HPLC RT [min] | M + H [m/z] |
|---|---|---|---|---|---|---|---|---|---|---|---|
| I-1 | H | CH | 3-Br, 5-$CF_3$ | $CH_3$ | H | N | CH | CH | B | 1.410 | 473.0 |
| I-2 | H | CH | 3-Br, 5-$CF_3$ | $CH_2CF_3$ | H | N | CH | CH | A | 1.139 | 539.3 |
| I-3 | H | CH | 3-Br, 5-$SO_2CH_3$ | $CH_2$-(4-$OCH_3$—$C_6H_4$) | H | N | CH | CH | B | 1.394 | 589.1 |
| I-4 | H | CH | 3-Br, 5-$CF_3$ | $CH_2CF_3$ | H | CH | CH | CH | B | 1.563 | 540.0 |
| I-5 | H | CH | 3-Br, 5-$SO_2CH_3$ | $CH_2cC_3H_5$ | H | N | CH | CH | B | 1.306 | 523.1 |
| I-6 | $CH_2$-(2,2-$F_2$—$cC_3H_3$) | CH | 3-Br, 5-$SO_2CH_3$ | $C_2H_5$ | H | N | CH | CH | B | 1.369 | 587.2 |
| I-7 | H | CH | 3-Cl, 5-$CF_3$ | $C_6H_5$ | H | N | CH | CH | B | 1.548 | 489.2 |
| I-8 | $CH_3$ | CH | 3-Br, 5-$SO_2CH_3$ | $CH_3$ | H | N | CH | CH | C | 1.999 | 497.0 |
| I-9 | H | CH | 3-Cl, 5-$CF_3$ | $SO_2CH_3$ | H | N | CH | CH | B | 1.474 | 491.2 |
| I-10 | H | CH | 3,5-$(CF_3)_2$ | $CH_3$ | H | N | CH | CH | B | 1.409 | 461.2 |
| I-11 | H | CH | 3,5-$(CF_3)_2$ | $CH_2CF_3$ | H | N | CH | CH | B | 1.542 | 529.2 |
| I-12 | H | N | 3,5-$Cl_2$ | $C_2H_5$ | H | N | CH | CH | B | 1.257 | 408.2 |
| I-13 | H | CH | 3-Br, 5-$CF_3$ | $CH_2CF_3$ | H | CH | N | CH | B | 1.665 | 541.2 |
| I-14 | H | CH | 3-Cl, 5-$SO_2CH_3$ | $CH_2CF_3$ | H | CH | CBr | CH | B | 1.573 | 584.1 |
| I-15 | $CH_2$—$cC_3H_5$ | CH | 3,5-$(CF_3)_2$ | $CH_2CF_3$ | H | N | CH | CH | B | 1.651 | 583.3 |
| I-16 | H | CH | 3-Cl, 5-$CF_3$ | $CH_2CF_3$ | H | CH | CBr | CH | B | 1.857 | 574.1 |
| I-17 | H | CH | 3-Br, 5-$SO_2CH_3$ | $cC_3H_5$ | H | N | CH | CH | C | 2.067 | 509.0 |
| I-18 | H | CH | 3-Br, 5-$SO_2CH_3$ | $CH_3$ | 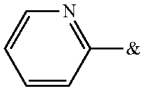 | N | CH | CH | B | 1.394 | 560.2 |
| I-19 | H | CH | 3-Br, 5-$OCF_3$ | $CH_2cC_3H_5$ | H | N | CH | CH | D | 2.842 | 527.1 |
| I-20 | H | CH | 3,5-$(CF_3)_2$ | $CH_2CHC{=}Cl_2$ | H | N | CH | CH | D | 3.043 | 555.1 |
| I-21 | H | CH | 3,5-$(CF_3)_2$ | $CH_2C(O)N(CH_3)C_2H_5$ | H | N | CH | CH | D | 2.607 | 546.2 |
| I-22 | H | CH | 3-Br, 5-CN | $CH_2cC_3H_5$ | H | N | CH | CH | D | 2.428 | 470.1 |
| I-23 | H | CH | 3-Cl, 5-$CF_3$ | $cC_3H_5$ | H | N | CH | CH | B | 1.542 | 453.2 |
| I-24 | H | CH | 3-Br, 5-$SO_2CH_3$ | $CH_2cC_3H_5$ | $CH_3$ | N | CH | CH | B | 1.400 | 537.2 |
| I-25 | H | CH | 3-Cl, 5-$CF_3$ | $CH_2CF_3$ | H | CH | CCl | CH | B | 1.836 | 528.2 |
| I-26 | H | CH | 3-[$SO_2$(4-F-$C_6H_4$)], 5-Cl | $cC_3H_5$ | H | N | CH | CH | B | 1.539 | 543.2 |
| I-27 | H | CH | 3-Br, 5-CN | $C_2H_5$ | H | N | CH | CH | D | 2.226 | 444.1 |
| I-28 | H | CH | 3-Br, 5-$OCF_3$ | $C_2H_5$ | H | N | CH | CH | D | 2.674 | 501.1 |
| I-29 | H | CH | 3,5-$(CF_3)_2$ | $CH_2$-(2,2-Cl—$cC_3H_3$) | H | N | CH | CH | C | 2.834 | 569.0 |
| I-30 | H | CH | 3-Cl, 5-$CF_3$ | $CH_2CF_3$ | H | CH | CCN | CH | B | 1.741 | 519.2 |
| I-31 | H | CH | 3-Cl, 5-$CF_3$ | $CH_2CF_3$ | H | CH | CH | CCl | B | 1.823 | 528.1 |
| I-32 | H | CH | 3-$CF_3$, 5-CN | $CH_2CF_3$ | H | CH | CCN | CH | B | 1.627 | 510.2 |
| I-33 | H | CH | 3-$CF_3$, 5-CN | $CH_2CF_3$ | H | CH | CH | CCN | B | 1.660 | 510.2 |
| I-34 | H | CH | 3-Cl, 5-$CF_3$ | $CH_2CF_3$ | H | CH | CH | CCN | B | 1.770 | 519.2 |
| I-35 | H | CH | 3-Cl, 5-$CF_3$ | $CH_2CF_3$ | H | CH | CH | N | B | 1.613 | 495.1 |
| I-36 | H | CH | 3-Br, 5-Cl | $C_2H_5$ | Cl | N | CH | CH | B | 1.667 | 487.0 |
| I-37 | $CH_2$—$cC_3H_5$ | CH | 3,5-$(CF_3)_2$ | $CH_3$ | 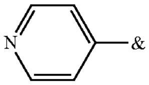 | N | CH | CH | A | 1.105 | 592.1 |
| I-38 | $CH_2$—$cC_3H_5$ | CH | 3,5-$(CF_3)_2$ | $C_6H_5$ | H | N | CH | CH | A | 1.328 | 577.3 |
| I-39 | $CH_2$—$cC_3H_5$ | CH | 3,5-$(CF_3)_2$ | $CH_3$ | 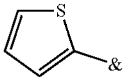 | N | CH | CH | A | 1.297 | 597.3 |

&denotes the bond to the remainder of the molecule

II. Evaluation of Pesticidal Activity

The activity of the compounds of formula I can be demonstrated and evaluated by the following biological tests.

B.1 Diamond Back Moth (*Plutella xylostella*)

The active compound was dissolved at the desired concentration in a mixture of 1:1 (vol:vol) distilled water: acetone. Surfactant (Kinetic HV) was added at a rate of 0.01% (vol/vol). The test solution was prepared on the day of use.

Leaves of cabbage were dipped in test solution and air-dried. Treated leaves were placed in petri dishes lined with moist filter paper and inoculated with ten 3rd instar larvae. Mortality was recorded 72 hours after treatment. Feeding damages were also recorded using a scale of 0-100%.

In this test, compounds I-1, I-2, I-4, I-5, I-7, I-9, I-10, I-11, I-12, I-13, I-15, and I-16, resp., at 300 ppm showed at least 75% mortality in comparison with untreated controls.

B.2 Green Peach Aphid (*Myzus persicae*)

For evaluating control of green peach aphid (*Myzus persicae*) through systemic means the test unit consisted of 96-well-microtiter plates containing liquid artificial diet under an artificial mem brane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds I-1, I-2, I-3, I-4, I-5, I-6, I-7, I-8, I-9, I-10, I-11, I-12, I-13, I-14, I-15, I-17, I-18, I-23, I-24, I-26, I-30, I-31, and I-32, resp., at 2500 ppm showed at least 75% mortality in comparison with untreated controls.

B.3 Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 μl, using a custom-built micro atomizer, at two replications.

After application, microtiter plates were incubated at about 28±1° C. and about 80±5% relative humidity for 5 days. Egg and larval mortality was then visually assessed.

In this test, compounds I-1, I-2, I-4, I-7, I-10, I-11, I-13, I-15, I-16, I-23, I-25, I-26, I-31, I-33, and I-38, resp., at 2500 ppm showed at least 75% mortality in comparison with untreated controls.

B.4 Boll Weevil (*Anthonomus grandis*)

For evaluating control of boll weevil (*Anthonomus grandis*) the test unit consisted of 96-well-microtiter plates containing an insect diet and 5-10 A. grandis eggs.

The compounds were formulated using a solution containing 75% v/v water and 25% v/v DMSO. Different concentrations of formulated compounds were sprayed onto the insect diet at 5 μl, using a custom-built micro atomizer, at two replications.

After application, microtiter plates were incubated at about 25±1° C. and about 75±5% relative humidity for 5 days. Egg and larval mortality was then visually assessed.

In this test, compounds I-1, I-2, I-4, 1-5, I-6, I-7, I-9, I-10, I-11, I-12, I-13, I-14, I-15, I-16, I-17, I-23, I-24, I-25, I-26, I-30, I-31, I-32, I-33, I-35, and I-38, resp., at 2500 ppm showed at least 75% mortality in comparison with untreated controls.

B.5. Southern Armyworm (*Spodoptera eridania*), 2nd Instar Larvae

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects. Lima bean plants (variety Sieva) were grown 2 plants to a pot and selected for treatment at the 1st true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. Ten to 11 armyworm larvae were placed into the bag and the bags zipped closed. Test plants were maintained in a growth room at about 25° C. and about 20-40% relative humidity for 4 days, avoiding direct exposure to fluorescent light (14:10 light:dark photoperiod) to prevent trapping of heat inside the bags. Mortality and reduced feeding were assessed 4 days after treatment, compared to untreated control plants.

In this test, compounds I-1, I-2, I-4, I-5, I-7, I-10, I-11, I-12, I-15, I-16, I-19, I-20, I-21, I-22, I-23, 1-25, and 1-26, resp., at 300 ppm showed at least 75% mortality in comparison with untreated controls.

B.6 Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult thrips. All test arenas were held under continuous light and a temperature of about 28° C. for duration of the assay. After 3 days, the numbers of live *thrips* were counted on each petal. The percent mortality was recorded 72 hours after treatment.

In this test, compounds I-1, I-2, I-9, I-10, I-15, and 1-17, resp., at 300 ppm showed at least 75% mortality in comparison with untreated controls.

The beneficial activity of the triazolone compounds according to the invention over structurally close compounds known from prior art with N-bonded triazoles was demonstrated by the following comparative experiments:

B.7 Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae.

The active compounds were formulated using a solution containing 75% (v/v) water and 25% (v/v) DMSO. Different concentrations of formulated compounds or mixtures were sprayed onto the insect diet at 2.5 μl, using a custom-built micro atomizer, at two replications.

After application, microtiter plates were incubated at 28±1° C., 80±5% RH for 2 days. Larval mortality was then visually assessed.

| Structure | Example | B.2, 10 ppm | B.6, 100 ppm |
|---|---|---|---|
| 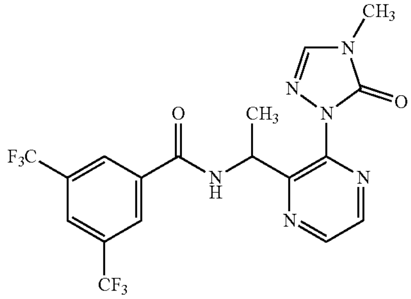 [SMILES: CC(NC(=O)c1cc(C(F)(F)F)cc(C(F)(F)F)c1)c1nccnc1-n1ncn(C)c1=O] | I-10 | 100 | 100 |
| 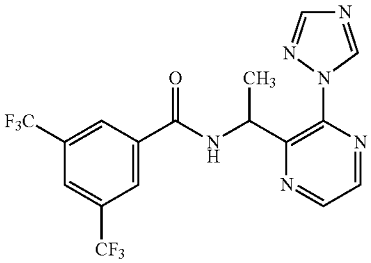 [SMILES: CC(NC(=O)c1cc(C(F)(F)F)cc(C(F)(F)F)c1)c1nccnc1-n1cncn1] | WO2021/037614 P46 | 25 | 0 |

| Structure | Example | B.2, 25 ppm | B.7, 10 ppm |
|---|---|---|---|
| 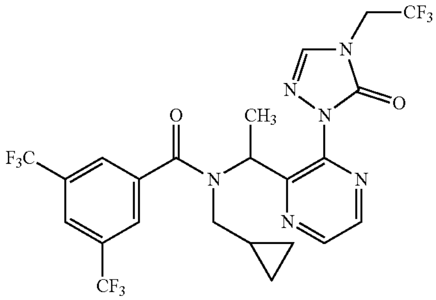 [SMILES: CC(c1nccnc1-n1ncn(CC(F)(F)F)c1=O)N(CC1CC1)C(=O)c1cc(C(F)(F)F)cc(C(F)(F)F)c1] | I-15 | 100 | 100 |
| 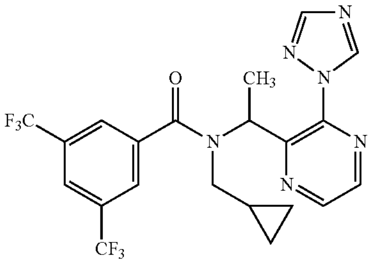 [SMILES: CC(c1nccnc1-n1cncn1)N(CC1CC1)C(=O)c1cc(C(F)(F)F)cc(C(F)(F)F)c1] | WO2021/037614 P48 | 50 | 0 |

The invention claimed is:

1. Compounds-A compound of formula I

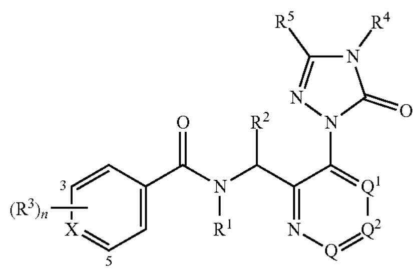

I wherein $R^1$ is H, OH, $C_1$-$C_6$-alkyl, $C_1$-$C_6$-haloalkyl, $C_3$-$C_6$-cycloalkyl, $C_3$-$C_6$-halocycloalkyl, $C_1$-$C_5$-alkoxy, $C_2$-$C_4$-alkenyl, $C_2$-$C_4$-alkynyl, $C_1$-$C_4$-alkyl-$C_3$-$C_6$-cycloalkyl, $C_1$-$C_4$-alkyl-$C_3$-$C_6$-halocycloalkyl, which groups are unsubstituted, or partially or fully substituted with $R^{11}$; or $C(=N-R^{11})R^{12}$, $C(O)R^{11a}$;

$R^{11}$ is CN, $NO_2$, $NR^{12}R^{13}$, $C(O)NH_2$, $C(S)NH_2$, C(O)OH, $OR^{14}$, $Si(CH_3)_3$; $C_1$-$C_6$-alkyl; $C_1$-$C_6$-haloalkyl; $C_2$-$C_6$-alkenyl; $C_2$-$C_6$-haloalkenyl; $C_2$-$C_6$-alkynyl; $C_2$-$C_6$-haloalkynyl; $C_3$-$C_4$-cycloalkyl-$C_1$-$C_2$-alkyl, which ring is unsubstituted or substituted with 1 or 2 halogen; 3- to 6-membered heterocyclyl, 5- or 6-membered hetaryl, or phenyl, which rings are unsubstituted or substituted with halogen, $C_1$-$C_3$-haloalkyl, and/or CN;

$R^{11a}$ is $NR^{12}R^{13}$, $C(O)NH_2$, $C(S)NH_2$, C(O)OH, $OR^{14}$, $Si(CH_3)_3$; $C_1$-$C_6$-haloalkyl; $C_2$-$C_6$-alkenyl; $C_2$-$C_6$-haloalkenyl; $C_2$-$C_6$-alkynyl; $C_2$-$C_6$-haloalkynyl; $C_3$-$C_6$-cycloalkyl-$C_1$-$C_2$-alkyl, which ring is unsubstituted or substituted with 1 or 2 halogen; 3- to 6-membered heterocyclyl, which rings are unsubstituted or substituted with halogen, $C_1$-$C_3$-haloalkyl, and/or CN;

$R^{12}$, $R^{13}$ are independently from each other H, $C_1$-$C_4$-alkyl, $C_1$-$C_4$-alkoxy, $C_1$-$C_4$-haloalkoxy, $C_1$-$C_4$-haloalkyl, $C_3$-$C_6$-cycloalkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, $C(O)NR^{121}R^{131}$, $S(O)_m$—$C_1$-$C_4$-haloalkyl, $S(O)_m$—$C_3$-$C_6$-cycloalkyl, $S(O)_m$—$C_3$-$C_6$-halocycloalkyl; 3- to 6-membered heterocyclyl, 5- or 6-membered hetaryl, or phenyl, which rings are unsubstituted or substituted with halogen, $C_1$-$C_3$-haloalkyl, and/or CN;

$R^{121}$ and $R^{131}$ are independently from each other H, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy; $C_1$-$C_4$-alkyl-phenyl, $C_1$-$C_4$-alkyl-3-6-membered hetaryl, phenyl, 3- to 6-membered heterocyclyl or 5- or 6-membered hetaryl, which rings are unsubstituted or substituted with halogen, $C_1$-$C_3$-haloalkyl, and/or CN; or $R^{121}$ and $R^{131}$ together with the nitrogen atom they are bound to form a 3-6 membered saturated, partially or fully unsaturated heterocycle, which may further contain 1 or 2 heteroatoms ring members selected from N, O and S, wherein S may be oxidized, which heterocycle is unsubstituted or substituted with halogen, $C_1$-$C_3$-haloalkyl, and/or CN;

or $R^{12}$ and $R^{13}$ together with the nitrogen atom they are bound to form a 3-6 membered saturated, partially unsaturated, or aromatic heterocycle, which may contain 1 or 2 additional heteroatoms selected from N, O and S, wherein S may be partially or fully oxidized, and which is unsubstituted or substituted with oxo, and/or $R^3$;

or $R^{12}$ and $R^{13}$ together with the nitrogen atom they are bound to form a group $N{=}S({=}O)R^{14a}R^{14b}$, wherein $R^{14a}$ and $R^{14b}$ are defined as $R^{14}$;

m is 0, 1, or 2;

$R^{14}$ is H, $C_1$-$C_4$-alkyl, $C_1$-$C_4$-haloalkyl, $C_3$-$C_6$-cycloalkyl, $C_3$-$C_6$-halocycloalkyl, $C_3$-$C_4$-cycloalkyl-$C_1$-$C_2$-alkyl, $C_3$-$C_4$-halocycloalkyl-$C_1$-$C_2$-alkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, or phenyl which is unsubstituted or partially or fully substituted with $R^3$;

$R^2$ is H, CN, $C_1$-$C_3$-alkyl, $C_1$-$C_3$-haloalkyl, $C_2$-$C_3$-alkynyl;

X is CH, $CR^3$, or N;

$R^3$ is halogen, CN, $NO_2$, $C_1$-$C_4$-alkyl, $C_3$-$C_6$-cycloalkyl, $C_1$-$C_6$-haloalkyl, $C_3$-$C_6$-halocycloalkyl, $OR^{14}$, $S(O)_m$—$R^{14}$; which are unsubstituted or substituted with $R^{3a}$;

$R^{3a}$ halogen, CN, $NO_2$, $C_1$-$C_4$-alkyl, $C_1$-$C_4$-haloalkyl, $C_1$-$C_4$-alkoxy-$C_1$-$C_4$-alkyl, $OR^{15}$, $C_1$-$C_4$-haloalkoxy, $C_3$-$C_4$-cycloalkyl, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl;

n is 0, 1, 2, or 3;

$R^4$ is $C_1$-$C_6$-alkyl, $C_3$-$C_6$-cycloalkyl, $C_1$-$C_6$-haloalkyl, $C_3$-$C_6$-halocycloalkyl, $C_2$-$C_4$-alkenyl, $C_2$-$C_4$-haloalkenyl, $C_2$-$C_4$-alkynyl, each unsubstituted or partially or fully substituted with $R^{41}$;

$S(O)_m$—$C_1$-$C_4$-alkyl, $S(O)_m$—$C_1$-$C_4$-haloalkyl, $S(O)_m$—$C_3$-$C_6$-cyclo-alkyl, $S(O)_m$—$C_3$-$C_6$-halocycloalkyl, $NR^{12}R^{13}$, $C(O)NR^{12}R^{13}$, $C(O)OR^{14}$, 3- to 6-membered heterocyclyl, 5- or 6-membered hetaryl, or phenyl, which rings are unsubstituted or partially or fully substituted with $R^3$;

$R^{41}$ is H, $OR^{15}$, $NR^{12}R^{13}$, $C_1$-$C_4$-alkyl, $C_1$-$C_4$-haloalkyl, $C_3$-$C_6$-cycloalkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, $C(O)OR^{15}$, $C(O)NR^{121}R^{131}$;

$S(O)_m$—$C_1$-$C_4$-haloalkyl, $S(O)_m$—$C_3$-$C_4$-cycloalkyl, $S(O)_m$—$C_3$-$C_4$-halocycloalkyl; 3- to 6-membered heterocyclyl, 5- or 6-membered hetaryl, or phenyl;

which cyclic $R^{41}$ groups are unsubstituted or partially or fully substituted with halogen, $C_1$-$C_3$-haloalkyl, and/or CN;

$R^{15}$ is H, $C_1$-$C_4$-alkyl, or $C_1$-$C_4$-haloalkyl, $C_3$-$C_6$-cycloalkyl, $C_1$-$C_6$-halocycloalkyl, which carbon chains are unsubstituted or partially or fully substituted with $R^{11}$; or 3- to 6-membered heterocyclyl, 5- or 6-membered hetaryl, or phenyl, which rings are unsubstituted or partially or fully substituted with $R^3$;

$R^5$ is H, halogen, CN, $OR^{15}$, $C_1$-$C_6$-alkyl, $C_1$-$C_6$-haloalkyl, $C_1$-$C_6$-alkoxy, $C_3$-$C_6$-cycloalkyl, $C_1$-$C_4$-alkyl-phenyl, $C_1$-$C_4$-alkyl-3-6-membered hetaryl, phenyl, 3- to 6-membered heterocyclyl or 5- or 6-membered hetaryl, which rings are unsubstituted or substituted with halogen, $C_1$-$C_3$-haloalkyl, and/or CN;

Q, $Q^1$, and $Q^2$ are, independently from each other, N or $CR^6$, wherein no more than one of Q, $Q^1$, and $Q^2$ is N;

$R^6$ is H, halogen, CN, $OR^{14}$, $NR^{12}R^{13}$, $C_1$-$C_4$-alkyl, $C_1$-$C_4$-haloalkyl, $C_3$-$C_6$-cycloalkyl, $C_3$-$C_6$-halocycloalkyl, $C(O)NR^{12}R^{13}$, $C(O)OR^{14}$, $S(O)_m$—$C_1$-$C_4$-alkyl, $S(O)_m$—$C_1$-$C_4$-haloalkyl, $S(O)_m$—$C_3$-$C_6$-cycloalkyl, $S(O)_m$—$C_3$-$C_6$-halocycloalkyl;

and N-oxides, stereoisomers, and agriculturally or veterinarily acceptable salts thereof.

2. The compound of formula I according to claim 1, wherein $R^{12}$, $R^{13}$ are independently from each other H, $C_1$-$C_4$-alkyl, $C_1$-$C_4$-alkoxy, $C_1$-$C_4$-haloalkoxy, $C_1$-$C_4$-haloalkyl, $C_3$-$C_6$-cycloalkyl, C(O)—$C_1$-$C_4$-alkyl, C(O)—$C_1$-$C_4$-haloalkyl, C(O)—$C_3$-$C_4$-cycloalkyl, C(O)—$C_3$-$C_4$-halocycloalkyl, $C(O)NR^{121}R^{131}$, $S(O)_m$—$C_1$-$C_4$-haloalkyl, $S(O)_m$—$C_3$-$C_6$-cycloalkyl, $S(O)_m$—$C_3$-$C_6$-halocycloalkyl; 3- to 6-membered heterocyclyl, 5- or 6-membered hetaryl, or phenyl, which rings are unsubstituted or substituted with halogen, $C_1$-$C_3$-haloalkyl, and/or CN;

$R^{121}$ and $R^{131}$ are independently from each other H, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy; $C_1$-$C_4$-alkyl-phenyl, $C_1$-$C_4$-alkyl-3-6-membered hetaryl, phenyl, 3- to 6-membered heterocyclyl or 5- or 6-membered hetaryl, which rings are unsubstituted or substituted with halogen, $C_1$-$C_3$-haloalkyl, and/or CN; or $R^{121}$ and $R^{131}$ together with the nitrogen atom they are bound to form a 3-6 membered saturated, partially or fully unsaturated heterocycle, which may further contain 1 or 2 heteroatoms ring members selected from N, O and S, wherein S may be oxidized, which heterocycle is unsubstituted or substituted with halogen, $C_1$-$C_3$-haloalkyl, and/or CN;

or $R^{12}$ and $R^{13}$ together with the nitrogen atom they are bound to form a 3-6 membered saturated, partially unsaturated, or aromatic heterocycle, which may contain 1 or 2 additional heteroatoms selected from N, O and S, wherein S may be partially or fully oxidized, and which is unsubstituted or substituted with $R^3$;

or $R^{12}$ and $R^{13}$ together with the nitrogen atom they are bound to form a group $N{=}S({=}O)R^{14a}R^{14b}$, wherein $R^{14a}$ and $R^{14b}$ are defined as $R^{14}$;

$R^3$ is halogen, CN, $NO_2$, $C_1$-$C_4$-alkyl, $C_3$-$C_6$-cycloalkyl, $C_1$-$C_6$-haloalkyl, $C_1$-$C_6$-halocycloalkyl, $OR^{14}$, $S(O)_m$—$R^{14}$; wherein rings are unsubstituted or substituted with $R^{3a}$;

$R^{3a}$ halogen, CN, $NO_2$, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy, $C_3$-$C_4$-cycloalkyl, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl;

n is 0, 1, 2, or 3;

$R^{41}$ is H, $OR^{15}$, $NR^{12}R^{13}$, $C_1$-$C_4$-alkyl, $C_1$-$C_4$-haloalkyl, $C_3$-$C_6$-cycloalkyl, C(O)—$C_1$-$C_4$-alkyl, C(O)—$C_1$-$C_4$-haloalkyl, C(O)—$C_3$-$C_4$-cycloalkyl, C(O)-$C_3$-$C_4$-halocycloalkyl, $C(O)NR^{121}R^{131}$;

$S(O)_m$—$C_1$-$C_4$-haloalkyl, $S(O)_m$—$C_3$-$C_4$-cycloalkyl, $S(O)_m$—$C_3$-$C_4$-halocycloalkyl; 3- to 6-membered heterocyclyl, 5- or 6-membered hetaryl, or phenyl; which cyclic $R^{41}$ groups are unsubstituted or partially or fully substituted with halogen, $C_1$-$C_3$-haloalkyl, and/or CN;

$Q^1$ and $Q^2$ are, independently from each other, N or $CR^6$;

$R^6$ is H, halogen, CN, $OR^{14}$, $NR^{12}R^{13}$, $C_1$-$C_4$-alkyl, $C_1$-$C_4$-haloalkyl, $C_3$-$C_6$-cycloalkyl, $C_3$-$C_6$-halocycloalkyl, $C(O)NR^{12}R^{13}$, $C(O)OR^{14}$, $S(O)_m$—$C_1$-$C_4$-alkyl, $S(O)_m$—$C_1$-$C_4$-haloalkyl, $S(O)_m$—$C_3$-$C_6$-cycloalkyl, $S(O)_m$—$C_3$-$C_6$-halocycloalkyl;

$Q^1$ and $Q^2$ are, independently from each other, N or $CR^6$, and Q is CH.

3. The compound of formula I according to claim 1, wherein $R^1$ is H.

4. The compound of formula I according to claim 1, wherein $R^2$ is $CH_3$.

5. The compound of formula I according to claim 1, wherein $R^3$ is halogen, CN, $C_1$-$C_4$-haloalkyl, $C_1$-$C_4$-haloalkoxy, $C_3$-$C_4$-cycloalkyl unsubstituted or substituted with one or more CN, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl, or $S(O)_m$—$R^{14}$, wherein $R^{14}$ is phenyl, which is partially substituted with $R^{3a}$.

6. The compound of formula I according to claim 1, wherein n is 2 and $R^3$ is in positions 3 and 5.

7. The compound of formula I according to claim 1, wherein X is CH.

8. The compound of formula I according to claim 1, wherein $R^4$ is $C_1$-$C_3$-alkyl, $C_3$-$C_6$-cycloalkyl, $C_1$-$C_3$-haloalkyl, $C_1$-$C_4$-alkoxy-$C_1$-$C_4$-alkyl, $CH_2C(O)NH$-$C_1$-$C_6$-alkyl, $S(O)_m$—$C_1$-$C_4$-alkyl, or phenyl unsubstituted or substituted with one or more groups $R^3$, wherein $R^3$ is halogen, CN, $C_1$-$C_4$-haloalkyl, $C_1$-$C_4$-haloalkoxy, $C_3$-$C_4$-cycloalkyl unsubstituted or substituted with one or more CN, $C_3$-$C_4$-halocycloalkyl, $S(O)_m$—$C_1$-$C_4$-alkyl, $S(O)_m$—$C_1$-$C_4$-haloalkyl, $S(O)_m$—$C_3$-$C_4$-cycloalkyl, $S(O)_m$—$C_3$-$C_4$-halocycloalkyl, or $S(O)_m$—$R^{14}$, wherein $R^{14}$ is phenyl, which is partially substituted with $R^{3a}$.

9. The compound of formula I according to claim 1, which corresponds to formula I.a I.a

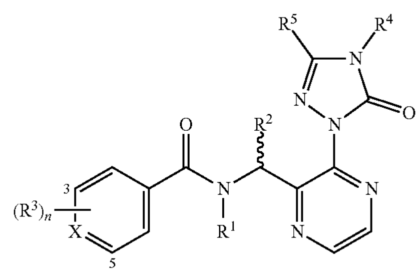

10. The compound of formula I according to claim 1, which corresponds to formula I.b, wherein $R^6$ is selected from the group consisting of H, halogen, and $C_1$-$C_4$-alkyl I.b

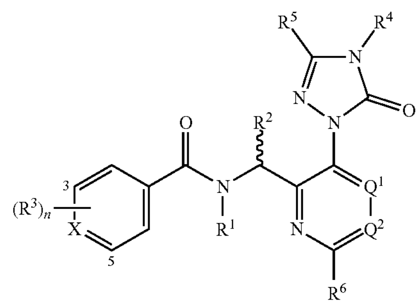

11. The compound of formula I according to claim 10, wherein $R^6$ is selected from the group consisting of H, halogen, and $C_1$-$C_4$-alkyl.

12. The compound of formula I according to claim 1, which is mainly isomer I.A

I.A

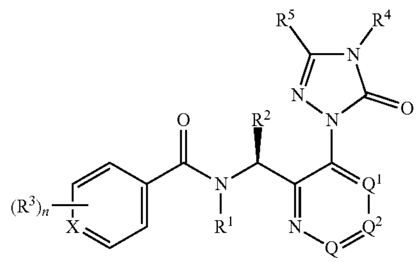

13. An intermediate compound of formula INT wherein the variables are as defined for formula I in claim 1

INT

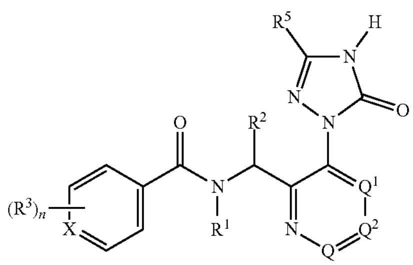

14. An agricultural or veterinary composition comprising at least one compound according to claim 1 and/or at least one agriculturally or veterinarily acceptable salt thereof, and at least one inert liquid and/or solid agriculturally or veterinarily acceptable carrier.

15. An agricultural composition for combating animal pests comprising at least one compound as defined in claim 1 and at least one inert liquid and/or solid acceptable carrier and, optionally, at least one surfactant.

16. A method for combating or controlling invertebrate pests, comprising contacting said pest or its food supply, habitat or breeding grounds with a pesticidally effective amount of at least one compound as defined in claim 1.

17. A method for protecting growing plants from attack or infestation by invertebrate pests, comprising contacting a plant, or soil or water in which the plant is growing, with a pesticidally effective amount of at least one compound as defined in claim 1.

18. A seed comprising a compound as defined in claim 1, or enantiomers, diastereomers, or salts thereof, in an amount of from 0.1 g to 10 kg per 100 kg of seed.

19. A method for treating or protecting an animal from infestation or infection by invertebrate pests comprising bringing the animal in contact with a pesticidally effective amount of at least one compound of the formula I as defined in claim 1, a stereoisomer thereof and/or at least one veterinarily acceptable salt thereof.

* * * * *